US011135321B2

(12) United States Patent
Khachaturian et al.

(10) Patent No.: US 11,135,321 B2
(45) Date of Patent: Oct. 5, 2021

(54) AUTOMATED RADIOPHARMACEUTICAL PRODUCTION AND QUALITY CONTROL SYSTEM

(71) Applicant: Best ABT, Inc., Springfield, VA (US)

(72) Inventors: Mark Khachaturian, Knoxville, TN (US); Doug Ferguson, Clinton, TN (US); Aaron McFarland, Knoxville, TN (US); Atilio Anzellotti, Knoxville, TN (US); Clive Brown-Proctor, Knoxville, TN (US)

(73) Assignee: Best Medical International, Inc., Springfield, VA (US)

( * ) Notice: Subject to any disclaimer, the term of this patent is extended or adjusted under 35 U.S.C. 154(b) by 553 days.

(21) Appl. No.: 14/618,795

(22) Filed: Feb. 10, 2015

(65) Prior Publication Data

US 2015/0238918 A1 Aug. 27, 2015

Related U.S. Application Data

(63) Continuation-in-part of application No. 13/446,334, filed on Apr. 13, 2012, which is a continuation-in-part of application No. 12/565,544, filed on Sep. 23, 2009, now Pat. No. 8,333,952, and a continuation-in-part of application No. 12/565,552, filed on Sep. 23, 2009, now abandoned.

(51) Int. Cl.
| | |
|---|---|
| *A61K 51/00* | (2006.01) |
| *A61M 36/14* | (2006.01) |
| *A61K 51/04* | (2006.01) |
| *B01J 19/00* | (2006.01) |
| *G01N 30/88* | (2006.01) |
| *G01N 30/00* | (2006.01) |

(52) U.S. Cl.
CPC ....... *A61K 51/0491* (2013.01); *B01J 19/0093* (2013.01); *B01J 2219/00788* (2013.01); *B01J 2219/00873* (2013.01); *B01J 2219/00891* (2013.01); *B01J 2219/00905* (2013.01); *G01N 2030/77* (2013.01); *G01N 2030/8872* (2013.01)

(58) Field of Classification Search
CPC .............. A61K 51/0491; B01J 19/0093; B01J 2219/00891; B01J 2219/00788; B01J 2219/00873; B01J 2219/00905; G01N 2030/8872; G01N 2030/77
USPC ....................................................... 424/1.89
See application file for complete search history.

(56) References Cited

U.S. PATENT DOCUMENTS

| | | |
|---|---|---|
| 4,187,076 A | 2/1980 | Elsohly et al. |
| 7,235,216 B2 | 6/2007 | Kiselev et al. |
| 8,080,815 B2 | 12/2011 | Nutt |
| 2002/0048536 A1 | 4/2002 | Bergh et al. |
| 2005/0232861 A1 | 10/2005 | Buchanan et al. |
| 2006/0253259 A1 | 11/2006 | Fernandez |
| 2007/0217963 A1* | 9/2007 | Elizarov ............. B01F 11/0042 422/130 |
| 2008/0067413 A1 | 3/2008 | Nutt et al. |
| 2008/0233018 A1 | 9/2008 | Van Dam et al. |
| 2008/0242915 A1* | 10/2008 | Jackson .................... G01T 1/00 600/4 |
| 2009/0036668 A1 | 2/2009 | Elizarov et al. |
| 2009/0162278 A1 | 6/2009 | Ravn et al. |
| 2010/0127188 A1* | 5/2010 | Nutt ....................... G21G 1/001 250/491.1 |
| 2010/0145630 A1 | 6/2010 | Ball et al. |
| 2011/0070158 A1* | 3/2011 | Nutt ................... A61K 51/0491 424/1.73 |
| 2011/0070160 A1 | 3/2011 | Nutt et al. |
| 2011/0150714 A1* | 6/2011 | Elizarov .............. B01J 19/0093 422/159 |
| 2011/0178359 A1 | 7/2011 | Hirschman et al. |
| 2013/0277566 A1 | 10/2013 | Giamis |

OTHER PUBLICATIONS

Crouzel C. et al, Radiopharmaceutical for Positron Emission Tomography, Methodological Aspects, Kluwer Academic Publishers, XP009135416.
9.1 Detectors, James M. Miller Chromatography—Concepts and Contrasts, 2005, Wiley-Interscience, XP-002708718.
J. Koziorowski et al.; A simple method for the quality control of [18F] FDG; Applied Radiation and Isotopes, www.elsevier.com/locate/apradiso.
Stephen M. Moerlein; Robotic preparation of sodium Acetate C11 injection for use in clinical PET, Nuclear Medicine and Biology 29 (2002) www.elsevier.com/locate/nucmedbio.
H. Denutte; Remote-controlled, Photosynthetic Preperation of HPLC-Purified [11C] Glucose; Int. J. Appl.Radiat. Isot. vol. 36 No. 1. pp. 82-84,1985.

(Continued)

*Primary Examiner* — Michael G. Hartley
*Assistant Examiner* — Sean R Donohue
(74) *Attorney, Agent, or Firm* — John C. Brosky; JanPaul Guzman; Laba Karki

(57) ABSTRACT

An automated radiopharmaceutical production and quality control system includes a particle accelerator, a radiopharmaceutical micro-synthesis subsystem, and quality control subsystem. The micro-accelerator of the improved biomarker generator is optimized for producing radioisotopes useful in synthesizing radiopharmaceuticals in quantities on the order of multiple unit doses, allowing for significant reductions in size, power requirements, and weight when compared to conventional radiopharmaceutical cyclotrons. The radiopharmaceutical micro-synthesis subsystem encompasses a small volume chemical synthesis system comprising a microreactor and/or a microfluidic chip and optimized for synthesizing the radiopharmaceutical in small quantities, allowing for significant reductions in processing time and in the quantity of radioisotope required. The automated quality control subsystem is used to test the composition and characteristics of the radiopharmaceutical to ensure that it is safe to inject.

20 Claims, 15 Drawing Sheets

(56) References Cited

OTHER PUBLICATIONS

G. Stoecklin: Qaulity Assurance and Qaulity Control of Short-Lived Radiopharmaceuticals for Pet, , Kluwer Academic Publishers, Radiopharamceuticals for Positron Emission.
S Yu, PhD, Review of 18 F-FDG synthesis and qaulity control, Biomedical Imaging and Intervention Journal.
Patent Cooperation Treaty; International Search Report; From PCT/ISA/220; dated Jun. 9, 2016.

\* cited by examiner

AUTOMATED RADIOPHARMACEUTICAL PRODUCTION AND QUALITY CONTROL SYSTEM

CROSS-REFERENCE TO RELATED APPLICATIONS

This application is a continuation-in-part of U.S. patent application Ser. No. 13/446,334, filed Apr. 13, 2012, which is a continuation-in-part of U.S. patent application Ser. No. 12/565,544, filed Sep. 23, 2009, now U.S. Pat. No. 8,333,952, and a continuation-in-part of U.S. patent application Ser. No. 12/565,552, filed Sep. 23, 2009. The contents of all of the foregoing applications are incorporated herein by reference.

STATEMENT REGARDING FEDERALLY-SPONSORED RESEARCH OR DEVELOPMENT

Not Applicable

BACKGROUND OF THE INVENTION

1. Field of Invention

This invention relates to a method and apparatus for automatically producing of radiopharmaceuticals and the automatic quality control testing of said radiopharmaceuticals.

2. Description of the Related Art

Cyclotrons are used to generate high energy charged particle beams for purposes such as nuclear physics research and medical treatments. One area where cyclotrons have found particular utility is in the generation of radiopharmaceuticals, also known as biomarkers, for medical diagnosis by such techniques as positron emission tomography (PET). A conventional cyclotron involves a substantial investment, both in monetary and building resources. An example of one of the more compact conventional cyclotrons used for radiopharmaceutical production is the Eclipse RD developed by the company founded by the present inventor and now produced by Siemens. The self-shielded version of the Eclipse RD can be installed in a facility without a shielded vault. The minimum room size for housing the Eclipse RD is 7.31 m×7.01 m×3 m (24 ft×23 ft×10 ft). To support the approximately 29 300 kg (64 400 lbs) installed weight of a self-shielded Eclipse RD, the cyclotron room includes a concrete pad with a minimum thickness of 36 cm (14 in). In addition to a large size and weight, the power requirements often involve a dedicated and substantial electrical power system. The minimum electrical service required for the Eclipse RD is a 208 (±5%) VAC, 150 A, 3-phase service. Thus, medical facilities have a need for biomarkers, but the monetary, structural, and power requirements of conventional cyclotrons have historically made it impracticable for most hospitals and other medical facilities to produce biomarkers on-site.

The half-life of clinically important positron-emitting isotopes, i.e., radionuclides, relative to the time required to process a radiopharmaceutical is a significant factor in biomarker generation. The large linear dimensions of the reaction vessel in radiochemical synthesis systems commonly used in biomarker generators result in a small ratio of surface area-to-volume and effectively limit the heat transfer and mass transport rates and lengthens processing time. The four primary PET radionuclides, fluorine-18, carbon-11, nitrogren-13, and oxygen-15, have short half-lives (approximately 110 min, 20 min, 10 min, and 2 min, respectively).

Consider the case of the production of $[^{18}F]$2-fluoro-2-deoxy-D-glucose, commonly referred to as $[^{18}F]$FDG. Converting nucleophilic fluorine-18 ($[^{18}F]F^-$) into $[^{18}F]$FDG requires up to 45 min using one of the larger conventional radiochemical synthesis systems, such as the Explora $FDG_4$ radiochemistry module, originally developed by a company founded by the present inventor and now produced by Siemens. The processing time is significant with respect to the half-life of the radioisotope. Accordingly, the production yield fraction of a biomarker of a conventional radiopharmaceutical synthesis system is far from ideal, often limited to a range of approximately 50% to 60% of the component substances. For the Explora $FDG_4$, the processing time fraction is approximately 40% of the half-life of the $[^{18}F]F^-$ radioisotope.

Corrected to the end of bombardment, the Explora $FDG_4$ has an yield fraction of approximately 65%. The limitations of the larger conventional radiochemical synthesis systems are even more evident when preparing biomarkers that are labeled with the radioisotopes having shorter half-lives. A conventional radiopharmaceutical synthesis system is designed to process a significant quantity of radioactivity. For example, the Explora $FDG_4$ accepts up to 333 GBq (9000 mCi) of $[^{18}F]F^-$. During bombardment, a significant percentage of the newly generated radioisotope decays back to its original target state requiring extended bombardment times to produce a sufficient quantity of the radioisotope for use in a conventional radiopharmaceutical synthesis system. For example, the production of approximately 90 GBq (2400 mCi) of $[^{18}F]F^-$ requires a bombardment time of approximately 120 min using the Eclipse RD cyclotron. Even with efficient distribution networks, the short half-lives and low yields require production of a significantly greater amount of the biomarker than is actually needed for the intended use. In contrast, the radioactivity of a unit dose of a biomarker administered to a particular class of patient or subject for medical imaging is considerable smaller, generally ranging from 0.185 GBq to 0.555 GBq (5 mCi to 15 mCi) for human children and adults and from 3.7 MBq to 7.4 MBq (100 µCi to 200 µCi) for mice.

Recent advancements have led to the development of smaller reaction systems using microreaction or microfluidic technology. By reducing the linear dimensions of the reaction vessel used in the radiochemical synthesis system, the ratio of surface area-to-volume and, consequently, heat transfer and mass transport rates increases. The smaller size of the reaction vessels lends itself to replication allowing multiple reaction vessels to be placed in parallel to simultaneously process the biomarker. In addition to faster processing times and reduced space requirements, these smaller reaction systems require less energy.

As with any medical application involving the use of radioactive materials, quality control is important in the synthesis and use of PET biomarker radiopharmaceuticals, both to safeguard the patient and to ensure the effectiveness of the administered radiopharmaceutical. For example, for the synthesis of $[^{18}F]$FDG from mannose triflate, a number of quality control tests exist. The final $[^{18}F]$FDG product should be a clear, transparent solution, free of particulate impurities; therefore, it is important to test the color and clarity of the final radiopharmaceutical solution. The final radiopharmaceutical solution is normally filtered through a sterile filter before administration, and it is advisable to test the integrity of that filter after the synthesized radiopharmaceutical solution has passed through it. The acidity of the final radiopharmaceutical solution must be within acceptable limits (broadly a pH between 4.5 and 7.5 for [$^{18}$F]FDG, although this range may be different depending upon the application and the radiopharmaceutical tracer involved). The final radiopharmaceutical solution should be tested for the presence and levels of volatile organics, such as ethanol or methyl cyanide, that may remain from synthesis process. Likewise, the solution should be tested for the presence of crown ethers or other reagents used in the synthesis process, as the presence of these reagents in the final dose is problematic. Further, the radiochemical purity of the final solution should be tested to ensure that it is sufficiently high for the solution to be useful. Other tests, such as tests of radionuclide purity, tests for the presence of bacterial endotoxins, and tests of the sterility of the synthesis system, are known in the art.

At present, most or all of these tests are performed on each batch of radiopharmaceutical, which will contain several doses. The quality control tests are performed separately by human technicians, and completing all of the tests typically requires between 45 and 60 minutes.

In the radiopharmaceutical area, a 2005 article discusses production of 0.064 GBq (1.74 mCi) of [$^{18}$F]FDG, a quantity sufficient for several positron emission tomography (PET) imaging studies on mice, using an integrated microfluidic circuit as proof of principle for automated multistep synthesis at the nanogram to microgram scale. Chung-Cheng Lee, et al., *Multistep Synthesis of a Radiolabeled Imaging Probe Using Integrated Microfluidics*, Science, Vol. 310, no. 5755, (Dec. 16, 2005), pp. 1793, 1796. The authors conclude that their chemical reaction circuit design should eventually yield sufficiently large quantities (i.e., >100 mCi) of [$^{18}$F]FDG to produce multiple doses for use in PET imaging of humans. The commercially available NanoTek Microfluidic Synthesis System distributed by Advion Bio-Sciences, Inc., can synthesize [$^{18}$F]FDG 35 times faster than with conventional macrochemistry, which clearly represents a significant improvement in radiopharmaceutical processing time. However, such level of advancement has not been seen with the cyclotrons producing the radioisotopes used in radiopharmaceutical synthesis. However, such level of advancement has not been seen with the cyclotrons producing the radioisotopes used in radiopharmaceutical synthesis.

A conventional cyclotron used in the production of radioisotopes for synthesizing radiopharmaceuticals has significant power requirements. Typically, a conventional cyclotron for radiopharmaceutical production generates a beam of charged particles having an average energy in the range of 11 MeV to 18 MeV, a beam power in the range of 1.40 kW and 2.16 kW, and a beam current of approximately 120 µA. The weight of an electromagnet of such a conventional cyclotron for radiopharmaceutical production typically ranges between 10 tons and 20 tons. The Eclipse RD is an 11 MeV negative-ion cyclotron producing up to two particle beams each with a 40 µA beam current. The major power consuming components of a cyclotron are typically the magnet system power supply, the RF system amplifier, the ion source transformer, the vacuum system cryopump compressor, and the water system. Of these, the magnet system power supply and the RF system amplifier are the most significant. The operating power consumption of the Eclipse RD is specified at 35 kW. The standby power consumption of the Eclipse RD is specified at less than 7 kW. The magnet system of the Eclipse RD produces a mean field of 1.2 T using 3 kW of power. The RF system of the Eclipse RD has a maximum amplifier power of 10 kW. The ion source system of the Eclipse RD is specified for a maximum H$^-$ current of 2 mA.

FIG. 1 is a representative illustration of an array of dees in a conventional cyclotron. For simplicity, only two dees 12 are illustrated. However, there are typically four or more dees used. Cyclotrons having fewer dees require more turns in the ion acceleration path, a higher acceleration voltage, or both to energize the ions to the desired level. The dees 12 are positioned in the valley of a large electromagnet and enclosed in a vacuum tank. During operation of the cyclotron, an ion source 81 continuously generates ions 19 through the addition or subtraction of electrons from a source substance. As the ions 19 are introduced into the cyclotron at the center of the array of dees 12, they are exposed a strong magnetic field generated by opposing magnet poles 11 situated above and below the array of dees 12. A radio frequency (RF) oscillator applies a high frequency, high voltage signal to each of the dees 12 causing the charge of the electric potential developed across each of the dees 12 to alternate at a high frequency. Neighboring dees are given opposite charges such that ions 19 entering the gap between neighboring dees 12 see a like charge on the dee behind them and an opposite charge on the dee ahead of them, which results in acceleration (i.e., increasing the energy) of the ions 19. With each energy gain, the orbital radius of the ions 19 increases. The result is a stream of ions 19 following an outwardly spiraling path. The ions 19 ultimately exit the cyclotron as a particle beam 40 directed at a target 89.

FIG. 2 illustrates an exploded view of selected components of a representative conventional two-pole cyclotron using the concept of sector-focusing to constrain the vertical dimension of the accelerated particle beam. The cyclotron includes upper and lower yokes 54 that cooperatively engage when assembled to define an acceleration chamber and opposing upper and lower magnet poles 11. Each magnet pole 11 includes two wedge-shaped pole tips 32, commonly referred to as "hills" where the magnetic flux 58 is mostly concentrated. The recesses between the hills 32 are commonly referred to as "valleys" 34 where the gap between the magnet poles 11 is wider. As a consequence of the wider gap between the magnets poles 11, the magnetic flux density in the valleys 34 is reduced compared to the magnetic flux density in the hills 32. A dee 12 is located in each open space defined by the corresponding upper and lower valleys 34. Vertical focusing of the beam is enhanced by a large hill field-to-valley field. A higher ratio indicates stronger magnetic forces, which tends to confine the beam closer to the median plane of the cyclotron. In principle, a tighter confinement allows reduction of the gap between the magnet poles without increasing the danger of the beam striking the pole faces of the magnet. For a given amount of flux, a magnet with a smaller gap between the magnet poles requires less electrical power for excitation than a magnet with a larger gap between the magnet poles. Once the ions are extracted from the cyclotron and are no longer under the influence of the magnet poles 11, a beam tube 92 directs the particle beam 40 through a collimator 96, which refines the profile of the particle beam 40 for irradiation of the target substance 100 contained in the target 89.

An unfortunate by-product of radioisotope production is the generation of potentially harmful radiation. The radiation generated as a result of operating a cyclotron is attenuated to acceptable levels by a shielding system, several variants of which are well known in the prior art. At the extraction point of a positive ion cyclotron, interaction between the positive ions 19p and the extraction blocks 102 used to induce the positive ions 19p to exit the cyclotron generate prompt high-energy gamma radiation and neutron radiation, a byproduct of nuclear reactions that produce radioisotopes. At the target 89, the nuclear reaction that occurs as the particle beam 40 irradiates the target substance 100 contained therein to produce the desired radioisotope generates prompt high-energy gamma radiation and neutron radiation. Additionally, residual radiation is indirectly generated by the nuclear reaction that yields the radioisotope. During the nuclear reaction, neutrons are ejected from the target substance and when they strike an interior surface of the cyclotron, gamma radiation is generated. Finally, direct bombardment of components such as the collimator 96 and the target window 98 by the particle beam 40 generates induced high-energy gamma radiation. Thus, a cyclotron must be housed in a shielded vault or be self-shielded. Although commonly composed of layers of exotic and costly materials, shielding systems only can attenuate radiation; they cannot absorb all of the gamma radiation or other ionizing radiation.

Following irradiation by the cyclotron, the target substance is commonly transferred to a radioisotope processing system. Such radioisotope processing systems are numerous and varied and are well known in the prior art. The radioisotope processing system prepares the radioisotope for the tagging or labeling of molecules of interest to enhance the efficiency and yield of the radiopharmaceutical synthesis processes. For example, the radioisotope processing system may extract undesirable molecules, such as excess water or metals to concentrate or purify the target substance.

BRIEF SUMMARY OF THE INVENTION

An improved biomarker generator and a method suitable for efficiently producing short lived radiopharmaceuticals in quantities on the order of a ten unit doses and the associated quality control testing is described in detail herein and illustrated in the accompanying figures. The automated radiopharmaceutical production and quality control system includes a particle accelerator, a radiopharmaceutical micro-synthesis system, and an automated quality control system. The micro-accelerator of the improved biomarker generator is optimized for producing radioisotopes useful in synthesizing radiopharmaceuticals in quantities on the order of one unit dose allowing for significant reductions in size, power requirements, and weight when compared to conventional radiopharmaceutical cyclotrons. The radiopharmaceutical micro-synthesis system of the improved biomarker generator is a small volume chemical synthesis system comprising a microreactor and/or a microfluidic chip and optimized for synthesizing the radiopharmaceutical in quantities on the order of one unit dose allowing for significant reductions in the quantity of radioisotope required and the processing time when compared to conventional radiopharmaceutical processing systems. The automated quality control system simplifies radiopharmaceutical production by automatically performing the required quality control tests and generating a dose record to be used as a quality control record. The system is also self shielded such that the radiation field outside the shield is acceptable for radiation workers (<1 mrem/hr).

The improved biomarker generator includes a small, low-power particle accelerator (hereinafter "micro-accelerator") for producing approximately multiple unit doses of a radioisotope that is chemically bonded (e.g., covalently bonded or ionically bonded) to a specific molecule. The micro-accelerator produces per run a maximum quantity of radioisotope that is approximately equal to the quantity of radioisotope required by the radiopharmaceutical micro-synthesis system to synthesize a unit dose of biomarker. The micro-accelerator takes advantage of various novel features, either independently or in combination to reduce size, weight, and power requirements and consumption. The features of the micro-accelerator described allow production of a radioisotope with a maximum radioactivity of approximately 2.59 GBq (70 mCi) using a particle beam with an average energy in the range of 5 MeV to 18 MeV or in various sub-ranges thereof and a maximum beam power in the range of 50 W to 200 W.

One feature of the micro-accelerator is the use of permanent magnets to contain the ions during acceleration and eliminate the electromagnetic coils of the common to conventional radiopharmaceutical cyclotrons. Each of the permanent magnets and the dees are wedge-shaped and arranged into a substantially circular array. A series of collimator channels in selected dees initially direct the path of the ions introduced at the center of the array. After exiting the series of collimator channels, the ions travel through the main channels of the dees until the desired energy level is achieved. The permanent magnet cyclotron provides substantial improvements with respect to cost, reliability, size, weight, infrastructure requirements, and power requirements compared to conventional radiopharmaceutical cyclotrons.

Another feature of the micro-accelerator is the use of an improved radio frequency (RF) system powered by a rectified RF power supply. A rectified input supplies a high voltage transformer to supply power to the RF oscillator. The RF signal produced by the RF system is high peak-to-peak voltage at the resonant frequency of the RF oscillator enveloped by the line voltage frequency. The charged particles are only accelerated during a portion of the line voltage cycle. The resulting RF power supply compensates for reduced activity by increasing the current.

A still further feature of the micro-accelerator is the use of an internal target cyclotron where the target is located within the magnetic field and the particle beam irradiates the internal target while still within the magnetic field. This allows the magnet system to assist in containing harmful radiation related to the nuclear reaction that converts the target substance into a radioisotope and eliminates a major source of radiation inherent in a conventional positive-ion cyclotron. As a result, the micro-accelerator can take advantage of the benefits without a significant disadvantage normally associated with a positive particle beam. Beams of positively-charged particles generally are more stable than beams of negatively-charged particle because the reduced likelihood of losing an electron at the high velocities that charged particles experience in a cyclotron. Losing an electron usually causes the charged particle to strike an interior surface of the cyclotron and generate additional radiation. Minimizing the production of excess radiation reduces the amount of shielding required. Additionally, a positive ion cyclotron requires significantly less vacuum pumping equipment. Reducing the amount of shielding and vacuum pumping equipment reduces the size, weight, cost, complexity, power requirements, and power consumption of the cyclotron.

Through the use of microreactors and microfluidic chips, which have fast processing times and offer precise control over the various stages of a chemical process, the radiopharmaceutical micro-synthesis system provides a significant reduction in processing time that directly reduces the quantity of the radioisotope required to synthesize the desired biomarker.

The method for producing a radiopharmaceutical using the improved biomarker generator calls for providing a micro-accelerator, producing charged particles, accelerating the charged particles, and forming a particle beam to irradiate a target substance and produce a radioisotope. The improved biomarker generator allows operation using a volume of the target substance that is unusually small in the area of radiopharmaceutical production. After irradiation, the radioisotope and at least one reagent are transferred to the radiopharmaceutical micro-synthesis system. The radioisotope undergoes processing as necessary. Ultimately, the radiopharmaceutical micro-synthesis system combines the radioisotope with the reagent or reagents to synthesize the biomarker.

The system includes a radiopharmaceutical micro-synthesis system having at least one microreactor and/or microfluidic chip. Using the unit or precursory unit dose of the radioisotope and at least one reagent, the radiopharmaceutical micro-synthesis system synthesizes on the order of a unit dose of a biomarker. Chemical synthesis using microreactors or microfluidic chips (or both) is significantly more efficient than chemical synthesis using conventional macroscale chemical synthesis technology. Yields are higher and reaction times are shorter, thereby significantly reducing the quantity of radioisotope required in synthesizing a unit dose of biomarker. Accordingly, because the micro-accelerator only produces relatively small quantities of radioisotope per production run, the maximum beam power of the micro-accelerator is approximately two to three orders of magnitude less than the beam power of a conventional particle accelerator. As a direct result of this dramatic reduction in maximum beam power, the micro-accelerator is significantly smaller and lighter than a conventional particle accelerator, has less stringent infrastructure requirements, and requires far less electricity. Additionally, many of the components of the small, low-power accelerator are less costly and less sophisticated, such as the magnet, magnet coil, vacuum pumps, and power supply, including the RF oscillator.

The synergy that results from combining the micro-accelerator and the radiopharmaceutical micro-synthesis system having at least one microreactor and/or microfluidic chip cannot be overstated. This combination, which is the essence of the improved biomarker generator, provides for the production of approximately one unit dose of radioisotope in conjunction with the nearly on-demand synthesis of one unit dose of a biomarker. The improved biomarker generator is an economical alternative that makes in-house biomarker generation at the imaging site a viable option even for small regional hospitals.

As disclosed herein, in several example embodiments, the present general inventive concept comprises quality control systems incorporating high performance liquid chromatography (HPLC) to perform quality control testing on a radiopharmaceutical solution shortly after synthesis. In several embodiments, an HPLC-based quality control system according to the present general inventive concept makes efficient use of sample volume and is compatible with and able to test a variety of radioisotopes and radiopharmaceutical compounds. In several embodiments, the automated nature of an HPLC-based quality control system according to the present general inventive concept allows for quality control tests to be conducted quickly and with minimal impact on user workflow. Overall, and especially when used as part of an integrated PET biomarker radiopharmaceutical production system as described herein, the present general inventive concept permits a radiopharmaceutical manufacturer to produce product and conduct quality control tests on the product with lower per dose costs.

An accelerator produces per run a maximum quantity of radioisotope that is approximately equal to the quantity of radioisotope required by the microfluidic chemical production module to synthesize a unit dose of biomarker. Chemical synthesis using microreactors or microfluidic chips (or both) is significantly more efficient than chemical synthesis using conventional (macroscale) technology. Percent yields are higher and reaction times are shorter, thereby significantly reducing the quantity of radioisotope required in synthesizing a unit dose of radiopharmaceutical. Accordingly, because the accelerator is for producing per run only such relatively small quantities of radioisotope, the maximum power of the beam generated by the accelerator is approximately two to three orders of magnitude less than that of a conventional particle accelerator. As a direct result of this dramatic reduction in maximum beam power, the accelerator is significantly smaller and lighter than a conventional particle accelerator, has less stringent infrastructure requirements, and requires far less electricity. Additionally, many of the components of the small, low-power accelerator are less expensive than the comparable components of conventional accelerators. Therefore, it is feasible to use the low-power accelerator and accompanying CPM within the grounds of the site of treatment. Because radiopharmaceuticals need not be synthesized at a central location and then transported to distant sites of treatment, less radiopharmaceutical need be produced, and different isotopes, such as carbon-11, may be used if desired.

If the accelerator and CPM are in the basement of the hospital or just across the street from the imaging center, then radiopharmaceuticals for PET can be administered to patients almost immediately after synthesis. However, eliminating or significantly reducing the transportation phase does not eliminate the need to perform quality control tests on the CPM and the resultant radiopharmaceutical solution itself. Still, it is essential to reduce the time required to perform these quality control tests in order to take advantage of the shortened time between synthesis and administration. The traditional 45 to 60 minutes required for quality control tests on radiopharmaceuticals produced in macro scale is clearly inadequate. Further, since the accelerator and the CPM are producing a radiopharmaceutical solution that is approximately just one (1) unit dose, it is important that the quality control tests not use too much of the radiopharmaceutical solution; after some solution has been sequestered for testing, enough radiopharmaceutical solution must remain to make up an effective unit dose.

In one example embodiment of the present general inventive concept, a high-performance-liquid-chromatography-based quality control testing system to test a sample radiopharmaceutical solution comprises a high performance liquid chromatography column to receive a sample radiopharmaceutical solution. This high performance liquid chromatography column separates molecularly distinct species within the sample radiopharmaceutical solution into a number of separated molecularly distinct species. A refractive index detector measures the amount of each separated molecularly distinct species from said high performance liquid chromatography column, and a radiation detector measures the radioactivity of each separated molecularly distinct species from said high performance liquid chromatography column.

In one example embodiment of the present general inventive concept, an HPLC-based quality control testing system to test a sample radiopharmaceutical solution comprises a valve (in some embodiments, an injection valve) to direct the flow of a sample radiopharmaceutical solution within the system; a sample radiopharmaceutical solution pumping mechanism to direct the sample radiopharmaceutical solution to the valve; a first sample collection vessel to receive a first part of the sample radiopharmaceutical solution from said injection valve, said first sample collection vessel to hold the first part of the sample radiopharmaceutical solution for endotoxicity testing; a fluid loop in fluid communication with said injection valve, said fluid loop to receive a second part of the sample radiopharmaceutical solution; a high performance liquid chromatography column to receive the second part of the sample radiopharmaceutical solution, said high performance liquid chromatography column to separate molecularly distinct species within the second part of the sample radiopharmaceutical solution into a number of separated molecularly distinct species; a refractive index detector to measure the amount of each separated molecularly distinct species from said high performance liquid chromatography column; and a radiation detector to measure the radioactivity of each separated molecularly distinct species from said high performance liquid chromatography column. Often, some embodiments include a high performance liquid chromatography pump to direct a mobile phase solvent to the valve and the HPLC column. In some embodiments, an HPLC-based quality control testing system according to the present general inventive concept also comprises an ultraviolet-light detector or UV/VIS detector to measure the optical qualities of the second part of the sample radiopharmaceutical solution. In some embodiments, the ultraviolet-light detector or UV/VIS detector measures the optical qualities of the second part of the sample radiopharmaceutical solution before the second part of the sample radiopharmaceutical solution enters the high performance liquid chromatography column. Additionally, many embodiments of the present general inventive concept include a pH detector to measure the pH of the sample radiopharmaceutical solution. Further, in some embodiments, the system also includes an automated endotoxin detector to perform endotoxicity testing on the first part of the sample radiopharmaceutical solution held in the first sample collection vessel. In some embodiments, the automated endotoxin detector includes a kinetic hemocyte lysate-based assay.

In some embodiments, an HPLC-based quality control testing system according to the present general inventive concept includes a radiation detector that comprises at least two radiation probes, with a first radiation probe to measure the radioactivity of a part of the sample radiopharmaceutical solution that has not passed through said high performance liquid chromatography column and a second radiation probe to measure the radioactivity of each separated molecularly distinct species from said high performance liquid chromatography column.

In one example embodiment of the present general inventive concept, a method for conducting quality control tests in real time on a radiopharmaceutical comprises: introducing into a reaction vessel a radioisotope and at least one reagent for synthesis of a preselected radiopharmaceutical; reacting said radioisotope and said at least one reagent to produce said preselected radiopharmaceutical in a raw state radiopharmaceutical solution containing undesirable chemical entities; conveying said raw state radiopharmaceutical solution through at least one cleansing step wherein at least one undesirable chemical entity is removed from said radiopharmaceutical solution, whereby said radiopharmaceutical solution is clarified; conveying a portion of said clarified radiopharmaceutical solution to a radiopharmaceutical solution pumping mechanism; pumping said clarified radiopharmaceutical solution to an injection valve, said injection valve to direct the flow of said clarified radiopharmaceutical solution; directing a first aliquot of the clarified radiopharmaceutical solution into a first sample collection vessel, said first sample collection vessel to hold the first aliquot of the clarified radiopharmaceutical solution for measurement of the radioactivity of the clarified radiopharmaceutical solution; directing a second aliquot of the clarified radiopharmaceutical solution into a second sample collection vessel, said second sample collection vessel to hold the second aliquot of the sample radiopharmaceutical solution for endotoxicity testing; directing a third aliquot of the clarified radiopharmaceutical solution into a high performance liquid chromatography column, said high performance liquid chromatography column to separate molecularly distinct species within the third aliquot of the clarified radiopharmaceutical solution into a number of separated molecularly distinct species; measuring the optical qualities of the third aliquot of the sample radiopharmaceutical solution by means of an ultraviolet-light detector; using a refractive index detector to measure the amount of each separated molecularly distinct species from said high performance liquid chromatography column; and measuring the radioactivity of each separated molecularly distinct species from said high performance liquid chromatography column.

In some embodiments, the measurement of the radioactivity of each separated molecularly distinct species from said high performance liquid chromatography column is performed by means of a radiation detector, said radiation detector including at least two radiation probes, said at least two radiation probes including: a first radiation probe to measure the radioactivity of the first aliquot of the sample radiopharmaceutical solution held in said first sample collection vessel; and a second radiation probe to measure the radioactivity of each separated molecularly distinct species from said high performance liquid chromatography column. Further, some embodiments of the method described above include a step of measuring the pH of the clarified radiopharmaceutical solution.

In some embodiments of the present general inventive concept, the radioisotope is selected from the group consisting of carbon-11, nitrogen-13, oxygen-15, and fluorine-18. In some embodiments, the radiopharmaceutical is [$^{18}$F]-2-fluoro-2-deoxy-D-glucose (hereinafter [$^{18}$F]FDG).

In some embodiments of the present general inventive concept, an automated radiopharmaceutical production and quality control system for automatically producing a quantity of radiopharmaceutical on the order of ten unit doses includes a user interface in communication with a computer, said user interface enabling the selection of a selected radiopharmaceutical for production, selection being made on and recorded by said user interface, whereby said user interface communicates an identity of the selected radiopharmaceutical to a computer; a cyclotron in communication with said computer, said cyclotron to produce a radioisotope associated with said selected radiopharmaceutical, said cyclotron initiating production of the radioisotope upon receiving computer activating; and a chemical production subsystem to transfer, synthesize, and purify said radioisotope into a maximum quantity of a radiopharmaceutical on the order of up to ten unit doses using a disposable microfluidic radiopharmaceutical synthesis card system, said chemical production subsystem supplying said radiopharmaceutical into a syringe for injection, said chemical production subsystem supplying said radiopharmaceutical into a vial for separating said radiopharmaceutical into individual unit doses, and said chemical production subsystem transferring at least one small volume of less than 300 microliters of said radiopharmaceutical to an Automated Quality Control System for Radiopharmaceuticals, said Automated Quality Control System for Radiopharmaceuticals to test the radiopharmaceutical to ensure that it is safe for injection.

In some embodiments, said cyclotron produces said radioisotope associated with said selected radiopharmaceutical by locating a target substance in a magnetic field generated by said cyclotron and bombarding said target substance with said particle beam without said particle beam exiting said magnetic field.

In some embodiments, said radioisotope associated with said selected radiopharmaceutical is $^{18}F$, $^{11}C$, $^{124}I$, $^{13}N$, $^{15}O$, or $^{68}Ga$.

In some embodiments, said selected radiopharmaceutical is produced in a specified maximum quantity determined by level of radioactivity of said quantity, wherein said selected radiopharmaceutical and level of radioactivity is selected from the group consisting of [18F]2-fluoro-2-deoxy-D-glucose with a maximum radioactivity level of approximately 250 mCi, [18F]Sodium Flouride with a maximum radioactivity level of approximately 250 mCi, [18F]fluoromisonidazole with a maximum radioactivity level of approximately 170 mCi, [18F] 3'-deoxy-3'fluorothymidine with a maximum radioactivity level of approximately 170 mCi, [18F] fluorocholine with a maximum radioactivity level of approximately 60 mCi, [18F]Fallypride with a maximum radioactivity level of approximately 250 mCi, [18F]Florbetaben with a maximum radioactivity level of approximately 180 mCi, [18F]Florbetapir with a maximum radioactivity level of approximately 300 mCi, [18F]-fluoro-ethyl-tyrosine with a maximum radioactivity level of approximately 200 mCi, [18F]flutemetamol with a maximum radioactivity level of approximately 150 mCi, [18F] FDOPA with a maximum radioactivity level of approximately 200 mCi, [11C]Choline with a maximum radioactivity level of approximately 100 mCi, [11C]acetate with a maximum radioactivity level of approximately 450 mCi, [11C]N-Methylspiperone with a maximum radioactivity level of approximately 200 mCi, [11C]Carfentanil with a maximum radioactivity level of approximately 100 mCi, and [11C]Raclopride with a maximum radioactivity level of approximately 100 mCi.

In some embodiments, said cyclotron has a maximum beam power selected from the group consisting of 50 W, 75 W, 100 W, 125 W, 150 W, 175, and 200 W.

In some embodiments, said cyclotron produces the radioisotope associated with said selected radiopharmaceutical with a beam of charged particles having an average energy within a range selected from the group consisting of 5 MeV to 18 MeV, 5 MeV to 10 MeV, 7 MeV to 10 MeV, 8 MeV to 10 MeV, and 7 MeV to 18 MeV.

In some embodiments, said average energy of said charged particles is in the range of 5 MeV to 10 MeV.

In some embodiments, said charged particles are selected from the group consisting of protons and deuterons and wherein said average energy of said charged particles is in the range of 5 MeV to 10 MeV and said maximum beam power is 200 W.

In some embodiments, said computer prints out a dose record summarizing the results of the quality control test.

In some embodiments, said system simultaneously manages manufacture of said radioisotopes and said radiopharmaceutical production and said quality control.

In some embodiments, said system activates an ion source which generates a beam of charged particles accelerated through a magnetic and electric field to an energy greater than or equal to the nuclear binding energy of the target substance.

In some embodiments, said system selects a target substance for said radioisotope of said radiopharmaceutical.

In some embodiments, said charged particles hitting said target substance produces a selected radioisotope.

In some embodiments, said system generating a particle beam of charged particles with a maximum beam power of 200 W, said charged particles selected from the group consisting of protons and deuterons, said charged particles accelerated to an average energy at least equal to the nuclear binding energy of said target substance.

In some embodiments, said system produces said radioisotope in a maximum quantity per production run on the order of up to ten unit doses from said target substance by bombarding said target substance with said charged particles.

In some embodiments, the target substance associated with said radiopharmaceutical is moved into said beam of charged particles by said computer.

In some embodiments, said system receives said radioisotope from manual injection into said disposable microfluidic radiopharmaceutical synthesis card system.

In some embodiments, said system has a vacuum pump attached to the vent line of said disposable microfluidic radiopharmaceutical synthesis card system to remove vapor formation.

In some embodiments, said system has the capability to read an RF ID chip or bar code to identify said radiopharmaceutical associated with said dose synthesis card.

In some embodiments, said system has a shield around the cyclotron reducing the radiation field to acceptable levels (<1 mrem/hr).

The automated nature of an HPLC-based quality control system according to the present general inventive concept allows for quality control tests to be conducted quickly and with minimal impact on user workflow; the automated system relieves a technician from having to perform a number of the quality control tests. When used as part of an integrated PET biomarker radiopharmaceutical production system as described herein, the present general inventive concept permits a radiopharmaceutical manufacturer to produce product and conduct quality control tests on the product with lower per dose costs.

BRIEF DESCRIPTION OF THE SEVERAL VIEWS OF THE DRAWINGS

The above-mentioned features of the invention will become more clearly understood from the following detailed description of the invention read together with the drawings in which.

DETAILED DESCRIPTION OF THE INVENTION

Figure 1:
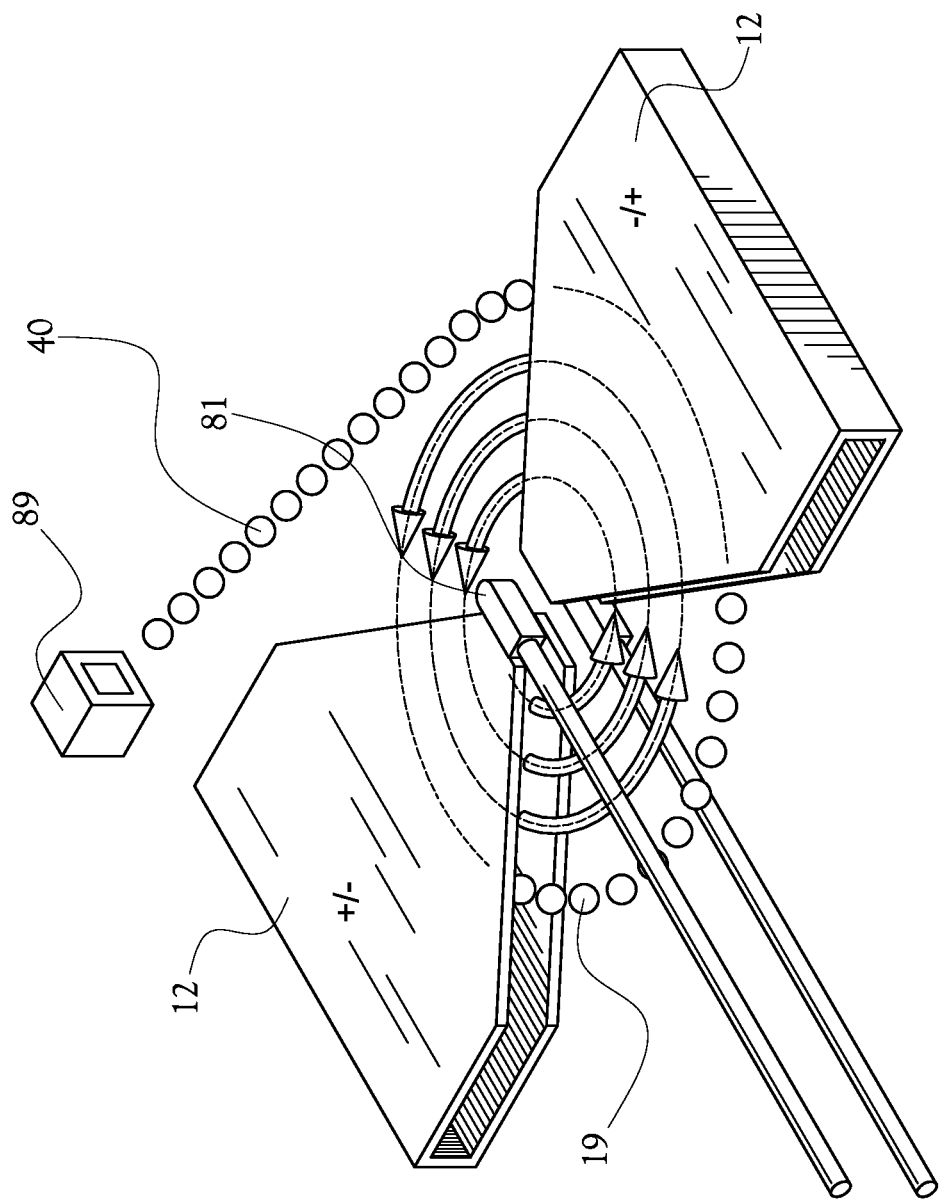
FIG. 1 is a perspective view of the ionization and acceleration components disposed within a conventional cyclotron.
Figure 2:
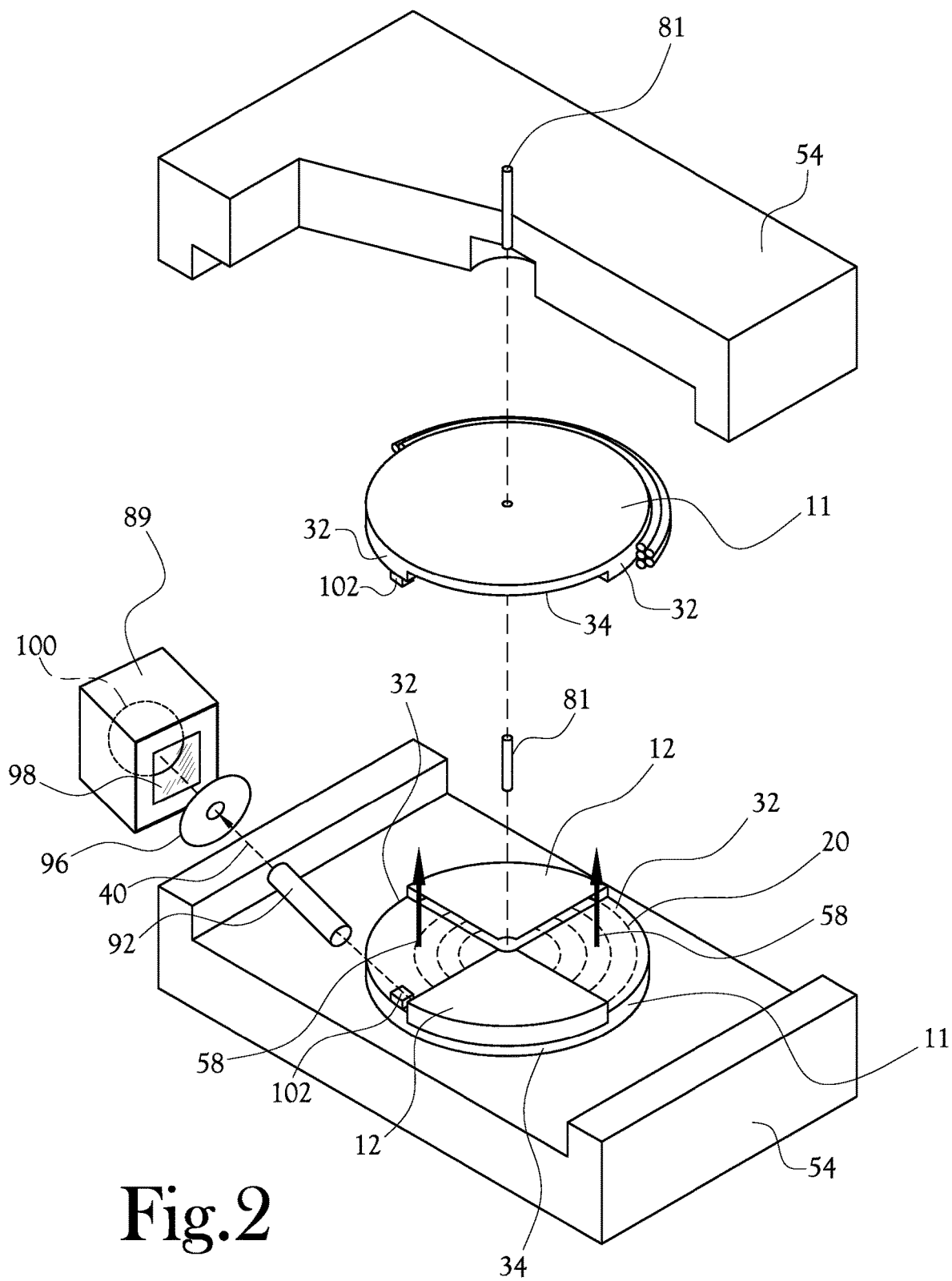
FIG. 2 is an exploded illustration of certain components of a prior art cyclotron.

An improved biomarker generator and a method suitable for efficiently producing short lived radiopharmaceuticals in quantities on the order of a unit dose is described in detail herein and illustrated in the accompanying figures. The improved biomarker generator includes a particle accelerator and a radiopharmaceutical micro-synthesis system. The micro-accelerator of the improved biomarker generator is optimized for producing radioisotopes useful in synthesizing radiopharmaceuticals in quantities on the order of one unit dose allowing for significant reductions in size, power requirements, and weight when compared to conventional radiopharmaceutical cyclotrons. The radiopharmaceutical micro-synthesis system of the improved biomarker generator is a small volume chemical synthesis system comprising a microreactor and/or a microfluidic chip and optimized for synthesizing the radiopharmaceutical in quantities on the order of one unit dose allowing for significant reductions in the quantity of radioisotope required and the processing time when compared to conventional radiopharmaceutical processing systems.

As used herein, "microreactors" and "microfluidic chips" refer broadly small volume reaction systems including microscale, nanoscale, and picoscale systems. As used herein, the term "radiopharmaceutical" encompasses any organic or inorganic compound comprising a covalently-attached radioisotope (e.g., 2-deoxy-2-[$^{18}$F]fluoro-D-glucose ([$^{18}$F]FDG)), any inorganic radioactive ionic solution (e.g., Na[$^{18}$F]F ionic solution), or any radioactive gas (e.g., [$^{11}$C]CO$_2$), particularly including radioactive molecular imaging probes intended for administration to a patient or subject (e.g., by inhalation, ingestion, or intravenous injection) for imaging purposes. Such probes are also referred to in the art as radiotracers and radioligands and, more generically, as radiochemicals. The terms "patient" and "subject" refer to any human or animal subject, particularly including all mammals. A "unit dose" refers to the quantity of radioactivity that is administered for medical imaging to a particular class of patient or subject. A unit dose of the radiopharmaceutical necessarily comprises a unit dose of a radioisotope.

As previously discussed, conventional radiopharmaceutical production focuses on generating a large amount of the radioisotope, typically on the order of Curies, in recognition of the significant radioactive decay that occurs during the relatively long time that the radioisotope undergoes processing and distribution. The improved biomarker generator of the present invention departs significantly from the established practice in that it is engineered to produce a per run maximum amount of radioisotope on the order of tens of millicuries. The micro-accelerator produces a maximum of approximately 2.59 GBq (70 mCi) of the desired radioisotope per production run. A particle accelerator producing a radioisotope on this scale requires significantly less beam power than conventional particle accelerators used for radiopharmaceutical production. The micro-accelerator generates a particle beam having a maximum beam power of 200 W. In various embodiments, the micro-accelerator generates a particle beam having a maximum beam power of approximately 200 W, 175 W, 150 W, 125 W, 100 W, 75 W, or 50 W. As a direct result of the dramatic reduction in maximum beam power, the micro-accelerator is significantly smaller and lighter than a conventional cyclotrons used in radiopharmaceutical production and requires less electricity. Many of the components of the micro-accelerator are less costly and less sophisticated compared to conventional cyclotrons used in radiopharmaceutical production.

Figure 3:
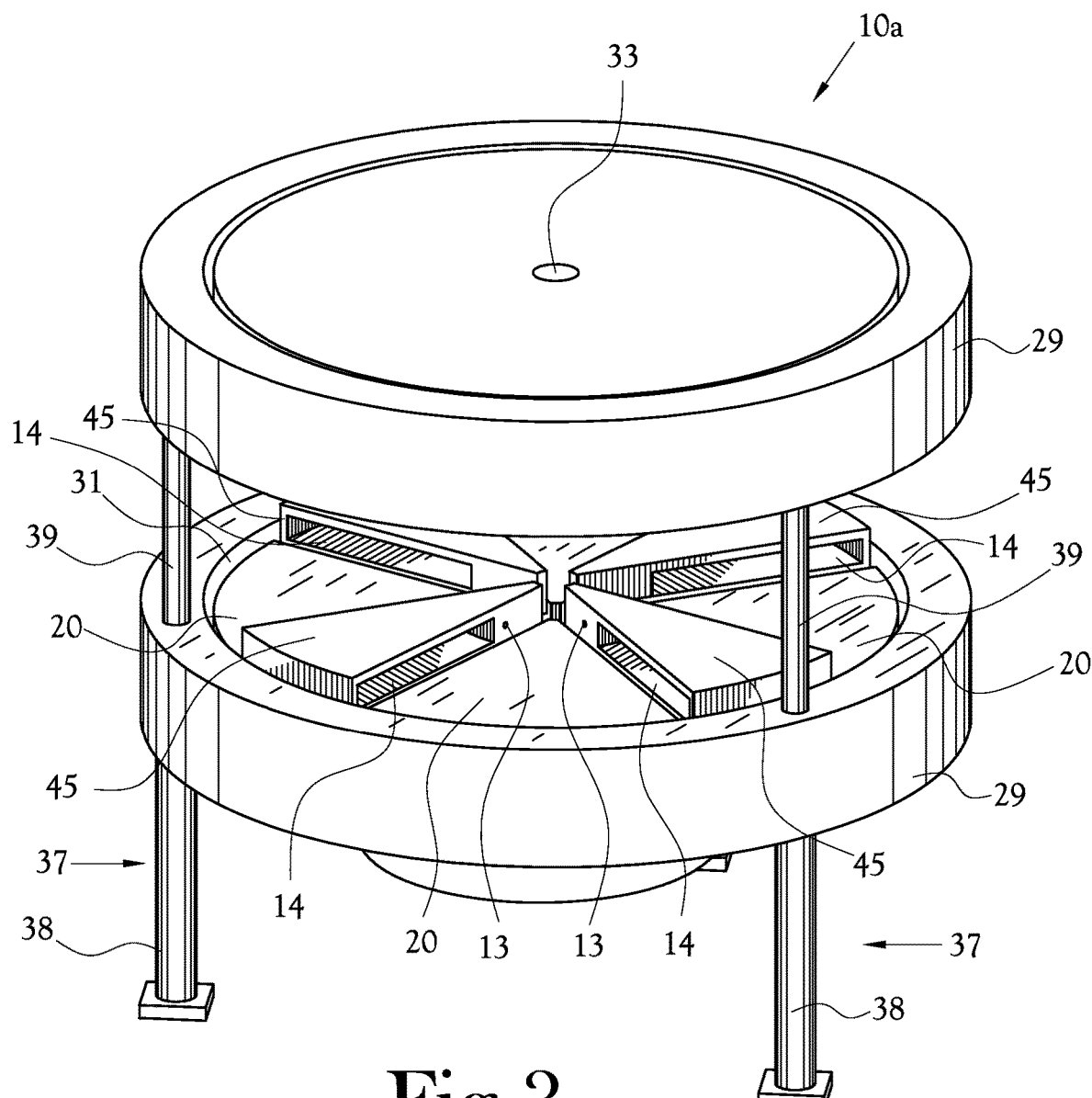
FIG. 3 is a perspective view one embodiment of a micro-accelerator suitable for use in the improved biomarker generator described herein, in the form of a cyclotron using permanent magnets, showing the micro-accelerator in an open configuration.
Figure 4:
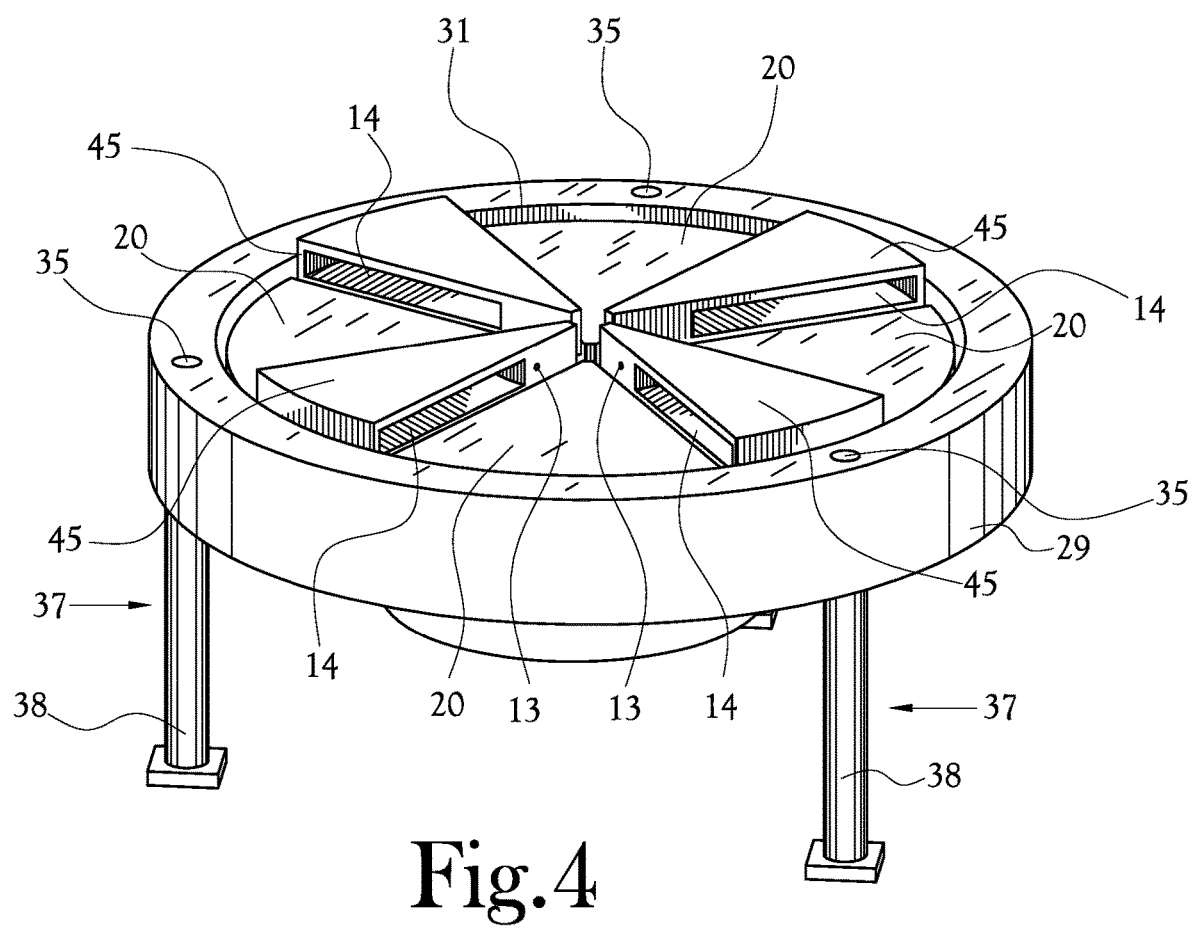
FIG. 4 is a perspective view of the lower platform of the micro-accelerator of FIG. 3.
Figure 5:
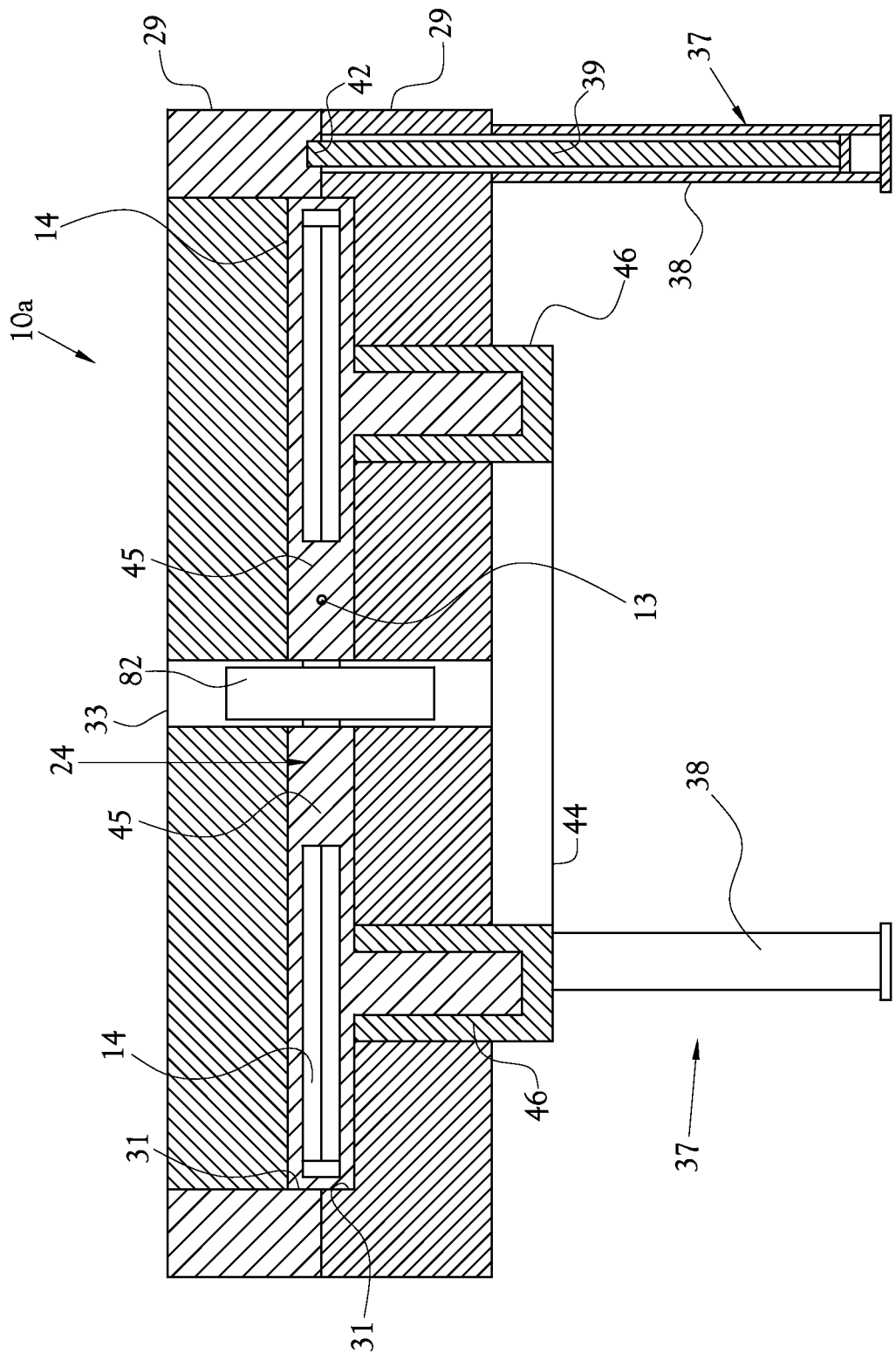
FIG. 5 is an elevation view, in cross-section taken along line 5-5 of FIG. 6, illustrating the micro-accelerator of FIG. 3 in a closed configuration.

FIG. 3 illustrates one embodiment of a selected portion of a micro-accelerator in the form of a cyclotron using permanent magnets 10a (hereinafter a "permanent magnet cyclotron") with the upper and lower platforms in an open configuration. FIG. 4 omits the upper platform to provide an unobstructed view of the components in the lower platform. FIG. 5 is a cross-sectional view of the micro-accelerator of FIG. 3 shown with the upper and lower platforms 29 in a closed configuration. Each of the upper and lower platforms 29 defines a cavity 31 on the interior side thereof, such that when the upper and lower platforms 29 are engaged, the cavities 31 define an acceleration chamber 27. A plurality of permanent magnets 20 are arranged in a circular array in the cavities of each of the upper and lower platforms 29 to form the magnet poles. Each permanent magnet 20 carried by the upper platform forms an opposing pair with the corresponding permanent magnet 20 carried by the lower platform. The valleys between the respective pairs of permanent magnets 20 are occupied by a plurality of dees 45, with one dee being disposed in each valley. A centrally located ion injection opening 33 is defined through the upper and lower platforms 29 allowing the ion source 82 to generate ions at the center of the circular array of dees 45 and permanent magnets 20. As shown in FIG. 5, the micro-accelerator includes an RF system 44 in electrical communication with each of the dees 45 via a plurality of through-openings defined by the lower platform. A dee support 46 attached to each dee 45 extends through a corresponding through-opening and electrically connects the attached dee to the RF system 44.

Each of the permanent magnets 20 and the dees 45 are wedge-shaped. Each permanent magnet 20 has a first end positioned proximate to the center of the array and a second positioned proximate to the periphery of the array. Likewise, each dee 45 has a first end positioned proximate to the center of the array and an second end positioned proximate to the periphery of the array. Each of the dees 45 defines a main channel 14 through which ions travel as they are accelerated. When the dees 45 are disposed with the valleys, the faces of the permanent magnet pole tips are disposed in substantially the same plane as the side of the of the corresponding horizontal member of the dees that define the main channel 14. In the illustrated embodiment, the horizontal inner surfaces of the dees are substantially co-planar with the corresponding pole faces of the magnet pairs. When the upper and lower platforms 29 are engaged, a magnet gap is defined between corresponding permanent magnets 20 of the upper and lower platforms 29. Accordingly, the entire channel has a substantially homogeneous height, which provides an unobstructed flight path for the ions being accelerated therein.

The upper and lower platforms 29 are supported by a plurality of legs 37. In the illustrated embodiment and best viewed in FIG. 5, each leg 37 is defined by the body of a pneumatic or hydraulic cylinder 38. The lower platform defines a plurality of through openings 35 for slidably receiving a piston rod 39 of each of the cylinders 38. The distal end 42 of each piston rod 39 is connected to the upper platform. Thus, engagement of the upper and lower platforms 29 is accomplished by retraction of the piston rods 39 into the respective cylinders 38. Separation of the upper and lower platforms 29 is accomplished by extending the piston rods 39 from within the cylinders 38. While this construction is disclosed, it will be understood that other configurations are contemplated as well.

Figure 6:
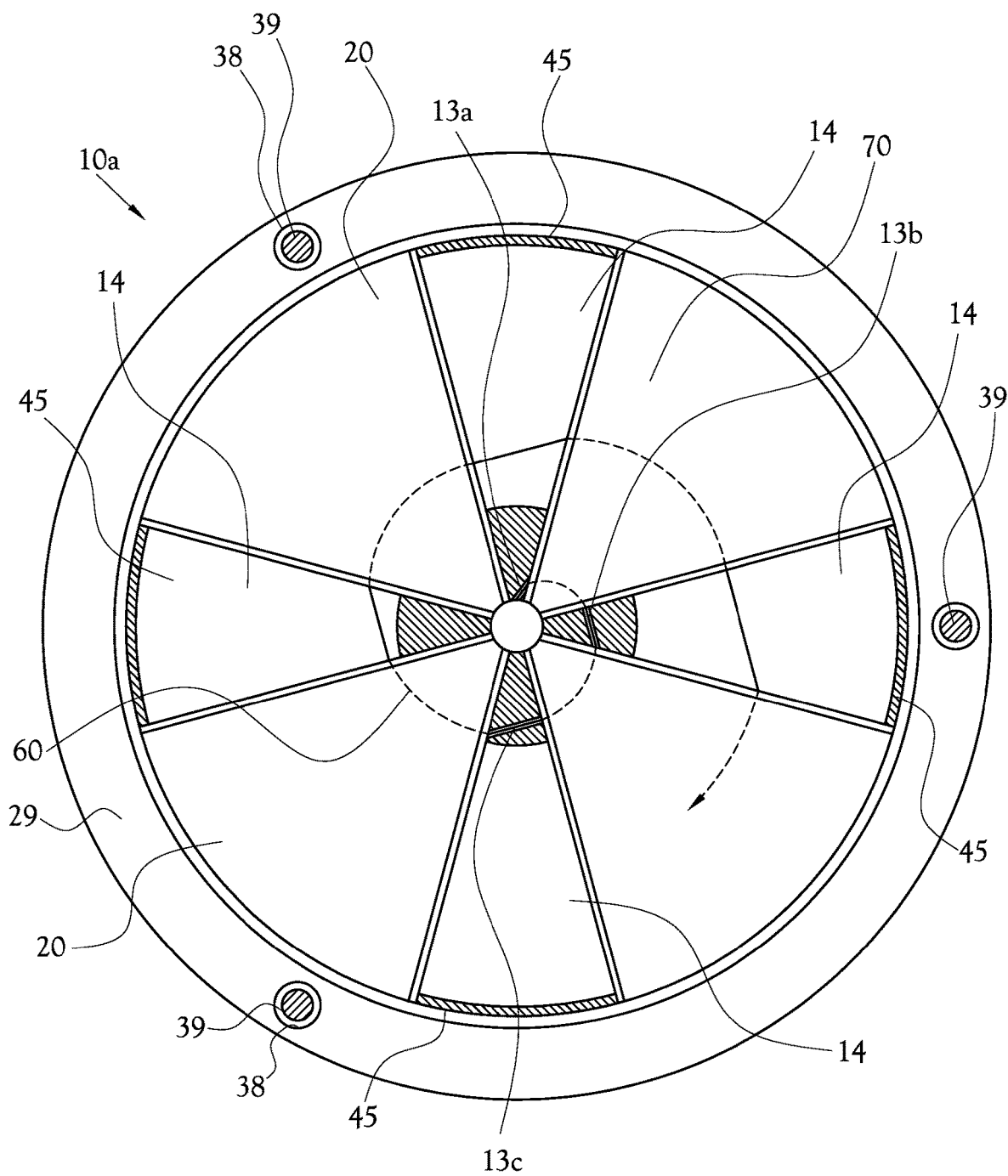
FIG. 6 is a plan view of the lower platform shown in FIG. 4 with the dees shown in cross-section to illustrate the flight path of the ions during acceleration.

FIG. 6 is a sectional top plan view of the permanent magnet cyclotron 10a showing the ion flight path 60. A series of collimator channels 13a, 13b, 13c are used to initially direct the path of the ions introduced at the center of the array. Each collimator channel 13a, 13b, 13c defines an outlet into the gap between corresponding permanent magnets 20 carried by the upper and lower platforms 29. In the illustrated embodiment, a first collimator channel 13a accepts ions introduced at the center of the array that are excited to a desired initial energy. Ions exiting the first collimator channel 13a travel along a generally arcuate course across the interposed hill and enter the second collimator channel 13b. Similarly, ions exiting the second collimator channel 13b travel across the interposed hill and enter the third collimator channel 13c. The first, second and third collimator channels 13a, 13b, 13c are configured to define the first revolution of the ions during acceleration. Ions that lack the desired initial energy level are rejected by not allowing such ions to enter the first collimator channel 13a. After exiting the third collimator channel 13c, the ions travel through the main channels 14 defined by each of the dees 45 until the desired energy level is achieved.

The permanent magnet cyclotron 10a provides substantial improvements with respect to cost and reliability when compared to conventional cyclotrons producing particle beams with energies of 10 MeV or less using electromagnets or superconducting magnets. Because the permanent magnet cyclotron 10a allows for the exclusion of the electromagnetic coils of the common to conventional radiopharmaceutical cyclotrons, the volume and weight are significantly reduced. In one embodiment, the volume and weight of the micro-accelerator are 40% of the volume and weight of conventional radiopharmaceutical cyclotrons, with a corresponding minimum equipment cost savings of approximately 25% of the equipment cost of conventional radiopharmaceutical cyclotrons. Additionally, eliminating the electric power needed to excite the electromagnet coils in a conventional cyclotron magnet significantly reduces the power requirements and realizes a significant savings in energy usage. The power requirements are further reduced as a result of the lower acceleration voltage of 8 MeV to 10 MeV or less applied to the dees. As a result of these improvements, the reliability of the permanent magnet cyclotron 10a is enhanced as compared to conventional radiopharmaceutical cyclotrons. As a result of the smaller size and lighter weight, more facilities are capable of operating the present invention, especially in situations where space is of concern. Further, because of the ultimately reduced purchase and operating costs, the permanent magnet cyclotron 10a is also more affordable. While the permanent magnet cyclotron 10a is presently not practical for higher acceleration voltages due to the increased magnetic field requirements of the permanent magnets, such embodiments are not excluded from the spirit of the present invention.

Figure 7:
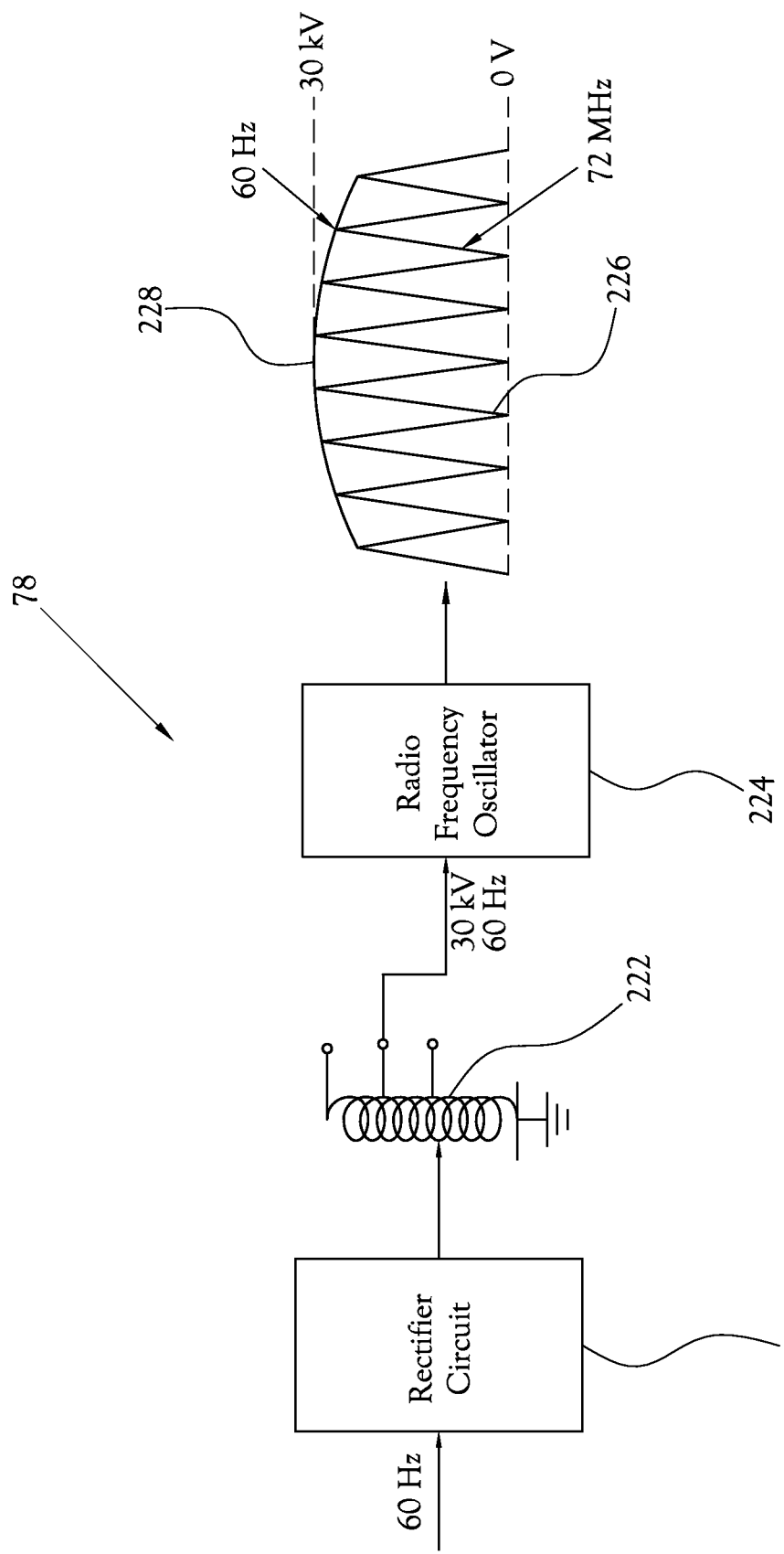
FIG. 7 illustrates one embodiment of radio frequency (RF) system for a micro-accelerator suitable for use in the improved biomarker generator described herein.

FIG. 7 is a block diagram of an improved RF system used in one embodiment of the micro-accelerator (hereinafter the "improved RF cyclotron"). The improved RF system includes a rectifier circuit 220 that accepts line voltage and produces a rectified voltage signal. The rectifier circuit 220 is a full wave rectifier incorporating two or more diodes, such as a dual diode rectifier. In one embodiment, the rectified voltage signal is the positive portion of the line voltage. The rectified voltage signal supplies the input of a high voltage step-up transformer 222 capable of supplying a high voltage and high current RF supply signal. In one embodiment, the step-up transformer is an autotransformer producing an output voltage of 30 kV at the line voltage frequency, e.g., 60 Hz. The RF oscillator 224 uses the RF supply signal to produce an RF signal at a selected frequency based on the resonance frequency of the RF oscillator 224 and having a peak-to-peak voltage corresponding to the peak voltage of the RF supply signal. The resonance frequency and the peak-to-peak voltage are selected to accelerate the charged particles to a selected energy level. The resulting RF signal drives the polarity of the dees to accelerate the charged particles. However, acceleration of positively charged particles occurs only during the positive portion of the 60 Hz cycle. By applying full wave rectification, the acceleration periods occur twice as often. For the production of radioisotopes useful in positron emission tomography imaging, only small amounts of radioactivity are necessary. By increasing the beam current, the improved RF cyclotron compensates for having acceleration during only a small portion of the 60 Hz cycle. In the illustrated embodiment, the resonance frequency of the RF oscillator is 72 MHz producing an RF signal having a frequency of 72 MHz with a maximum peak-to-peak voltage of 30 kV enveloped in the 60 Hz line voltage frequency.

To facilitate low-power operation, the ion source of one embodiment of the micro-accelerator is optimized for positive ion production. Beams of positively-charged particles generally are more stable than beams of negatively-charged particle because the reduced likelihood of losing an electron at the high velocities that charged particles experience in a cyclotron. Losing an electron usually causes the charged particle to strike an interior surface of the cyclotron and generate additional radiation. Minimizing the production of excess radiation reduces the amount of shielding required. Additionally, a positive ion cyclotron requires significantly less vacuum pumping equipment. Reducing the amount of shielding and vacuum pumping equipment reduces the size, weight, cost, complexity, power requirements, and power consumption of the cyclotron. In one embodiment, the ion source is optimized for proton ($H^+$) production. In an alternate embodiment, the ion source is optimized for deuteron ($^2H^+$) production. In another embodiment, ion source is optimized for alpha particle ($He^{2+}$) production.

Figure 8:
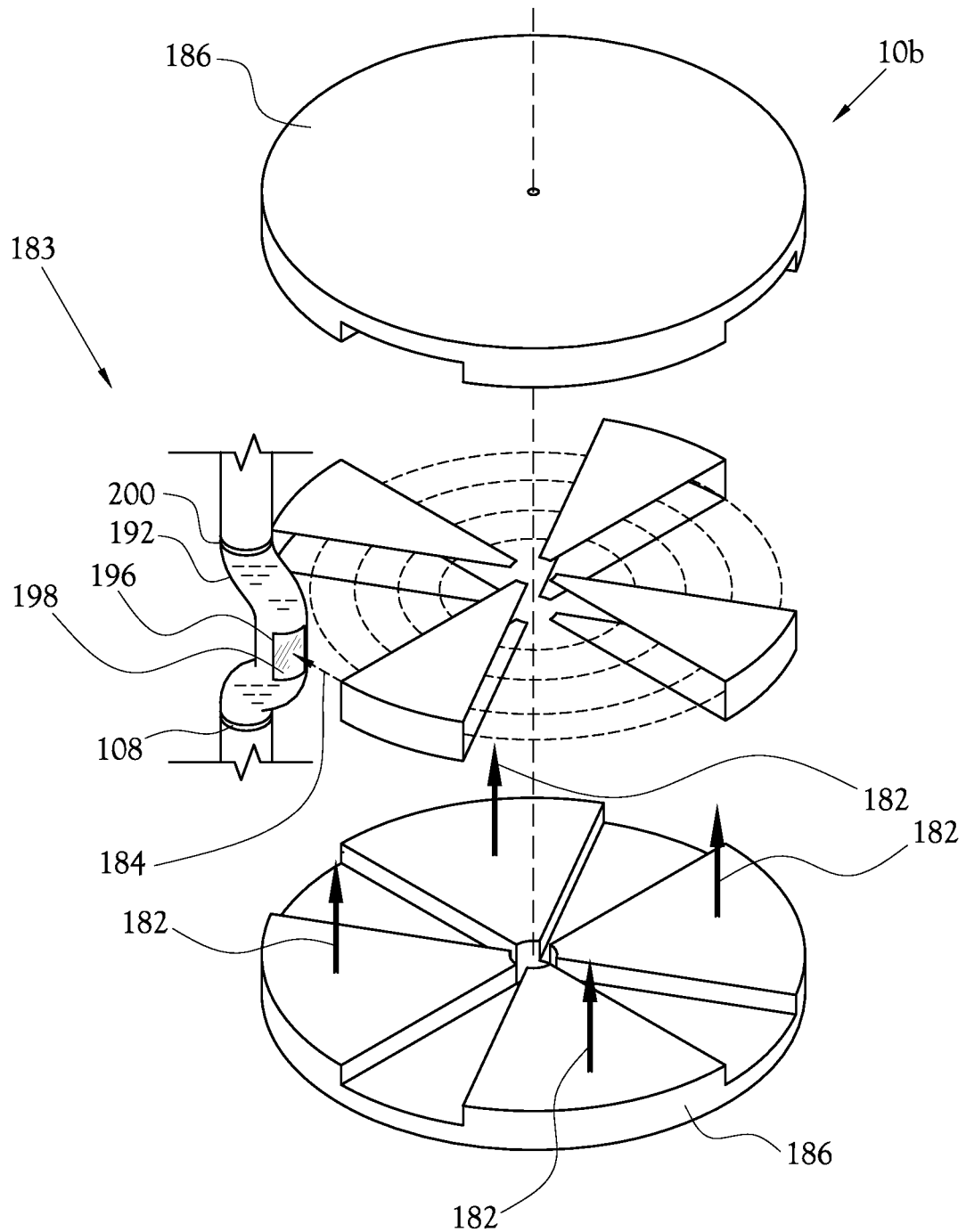
FIG. 8 is an exploded illustration of one embodiment of a micro-accelerator incorporating an internal target, suitable for use in the improved biomarker generator described herein.

FIG. 8 illustrates one embodiment of the micro-accelerator 10b in the form of a positive ion cyclotron (hereinafter "internal target cyclotron") where the target 183 (hereinafter "internal target") is located within the magnetic field. In this embodiment, the positive ion particle beam 184 irradiates the internal target 183 while still within the magnetic field 182 produced by the opposing magnet poles 186, 188. Consequently, the magnet system assists in containing harmful radiation related to the nuclear reaction that converts the target substance into a radioisotope. The internal target 183 eliminates a major source of radiation inherent in a conventional positive-ion cyclotron by eliminating the need for the conventional extraction blocks. In their absence, much less harmful radiation is generated. Thus, the internal target 183 eliminates a considerable disadvantage for positive-ion cyclotrons. A reduction in harmful radiation generation translates into a reduction in the amount of shielding and the associated benefits discussed above.

In the illustrated embodiment, the internal target 183 includes a stainless steel tube 192 that conducts the target substance. The stainless steel tube 192 has a target section centered in the path that the particle beam 184 travels following the final increment of acceleration. The longitudinal axis of the target section is substantially parallel to the magnetic field 182 generated by the magnet system and substantially perpendicular to the electric field generated by the RF system. The remainder of the stainless steel tube 192 is selectively shaped and positioned such that it does not otherwise obstruct the path followed by the particle beam 184 during or following its acceleration. The internal target 183 defines an opening 196 that is positioned in a path of the particle beam 184. A target window 198, which comprises a very thin layer of a foil such as aluminum, seals the opening 196 and prevents the target substance from escaping. Also, a pair of valves 200 control the flow of the target substance and hold a selected volume of the target solution in place for irradiation by the particle beam 184.

The diameter of the stainless steel tube 192 varies depending on the configuration of the internal target cyclotron 10b. Generally, the diameter is less than or equal to the increase in the orbital radius of the charged particles over one orbit, which in this embodiment is approximately four millimeters. Thus, in one embodiment, the diameter of the stainless steel tube 192 is approximately four millimeters. Because the charged particles gain a predetermined fixed quantity of energy that is manifested by an incremental fixed increase in the orbital radius of the beam, the charged particles do not interact with the stainless steel tube 192 prior to the final increment of acceleration, which would result in an undesirable situation that reduces the efficiency of the particle beam 184.

The micro-accelerator is designed to produce a particle beam in which the charged particles have an average energy sufficient to overcome the binding energy of the target isotope. In the area of radiopharmaceutical production, the minimum effective average energy of the charged particles is 5 MeV. Higher average particle energies result in more efficient radioisotope production and shorter production times. The micro-accelerator 112 produces a particle beam of charged particles with an average energy in the range of 5 MeV to 18 MeV. In one embodiment, the charged particles have an average energy in the range of 5 MeV to 10 MeV. In another embodiment, the charged particles have an average energy in the range of 7 MeV to 10 MeV. In another embodiment of the micro-accelerator 112, the charged particles have an average energy in the range of 8 MeV to 10 MeV. In yet another embodiment of the micro-accelerator 112, the charged particles have an average energy in the range of 7 MeV to 18 MeV. In more specific embodiments of the micro-accelerator 112, the charged particles are protons, deuterons, or alpha particles with an average energy in the range of 5 MeV to 18 MeV, 5 MeV to 10 MeV, 7 MeV to 10 MeV, 8 MeV to 10 MeV, or 7 MeV to 18 MeV. In a further embodiment, the micro-accelerator 112 generates a particle beam with a beam current of approximately 1 µA consisting essentially of protons having an energy of approximately 7 MeV, the particle beam having beam power of approximately 7 W and being collimated to a diameter of approximately 1 mm.

At lower average particle energies, fewer charged particles will be successful in destabilizing the target isotope and production time increases. As production time increases to a point that it is significant with respect to the half-life of the radioisotope, some of the radioisotope that has been produced will decay. The quantities of the radioisotope for which the micro-accelerator is designed are small enough to be practicable even when the ratio of production to decay is small. The various embodiments of the micro-accelerator are limited to producing a radioisotope with a maximum radioactivity of approximately 2.59 GBq (70 mCi) per production run. In one embodiment, the micro-accelerator produces a maximum of approximately 0.666 GBq (18 mCi) of fluorine-18 per production run. In another embodiment, the micro-accelerator produces a maximum of approximately 0.185 GBq (5 mCi) of fluorine-18 per production run. In yet another embodiment, the micro-accelerator produces a maximum of approximately 1.11 GBq (30 mCi) of carbon-11 per production run. In further embodiment, the micro-accelerator produces a maximum of approximately 1.48 GBq (40 mCi) of nitrogen-13 per production run. In still further embodiment, the micro-accelerator produces a maximum of approximately 2.22 GBq (60 mCi) of oxygen-15 per production run. Such embodiments of the micro-accelerator are flexible in that they can provide an adequate quantity of radioisotope for each of various classes of patients and subjects that undergo PET imaging.

The improved biomarker generator of the present invention may be embodied in many different forms. The permanent magnet cyclotron 10a, the improved RF cyclotron, and the internal target cyclotron 10b are examples of suitable components for use in a particle accelerator optimized as a micro-accelerator. Moreover, the various features of the permanent magnet cyclotron 10a, the improved RF cyclotron, and the internal target cyclotron 10b can be mixed and matched in a single micro-accelerator. Thus, one embodiment of the micro-accelerator is a combination of the permanent magnet cyclotron 10a with the internal target 183 of the internal target cyclotron 10b. Another embodiment of the micro-accelerator is a combination of the permanent magnet cyclotron 10a with the improved RF system. Yet another embodiment of the micro-accelerator is a combination of the internal target cyclotron 10b with the improved RF system. A still further embodiment is the combination of the permanent magnet cyclotron 10a with the improved RF system and the internal target 183 of the internal target cyclotron 10b.

Variations in the overall architecture of the micro-accelerator and the radiopharmaceutical micro-synthesis system are contemplated. For example, one embodiment, the micro-accelerator is a two-pole cyclotron. In another embodiment, the micro-accelerator is a four-pole cyclotron. Using a four-pole cyclotron may be advantageous in certain applications, because a four-pole cyclotron accelerates charged particles more quickly than a two-pole cyclotron using an equivalent accelerating voltage. The micro-accelerator described herein emphasizes the generation of a positively-charged particle beam; however, the acceleration of negatively-charged particles is necessary for certain applications and is considered within the scope of the present invention. The micro-accelerator described herein emphasizes the use of permanent magnets; however, the use of small electromagnets (weighing up to approximately 3 tons) is not outside the scope of the present invention for certain applications where a higher beam power is required. While the foregoing discussion emphasizes the use of a micro-accelerator, other types of particle accelerators may be used for production of the particle beam. Acceptable alternatives for the cyclotron include linear accelerators, radiofrequency quadrupole accelerators, and tandem accelerators. The production quantities, the ion source types, and the particle beam energies, ranges, diameters, particles, and powers apply to the various embodiments and modifications of the micro-accelerators.

Figure 9:
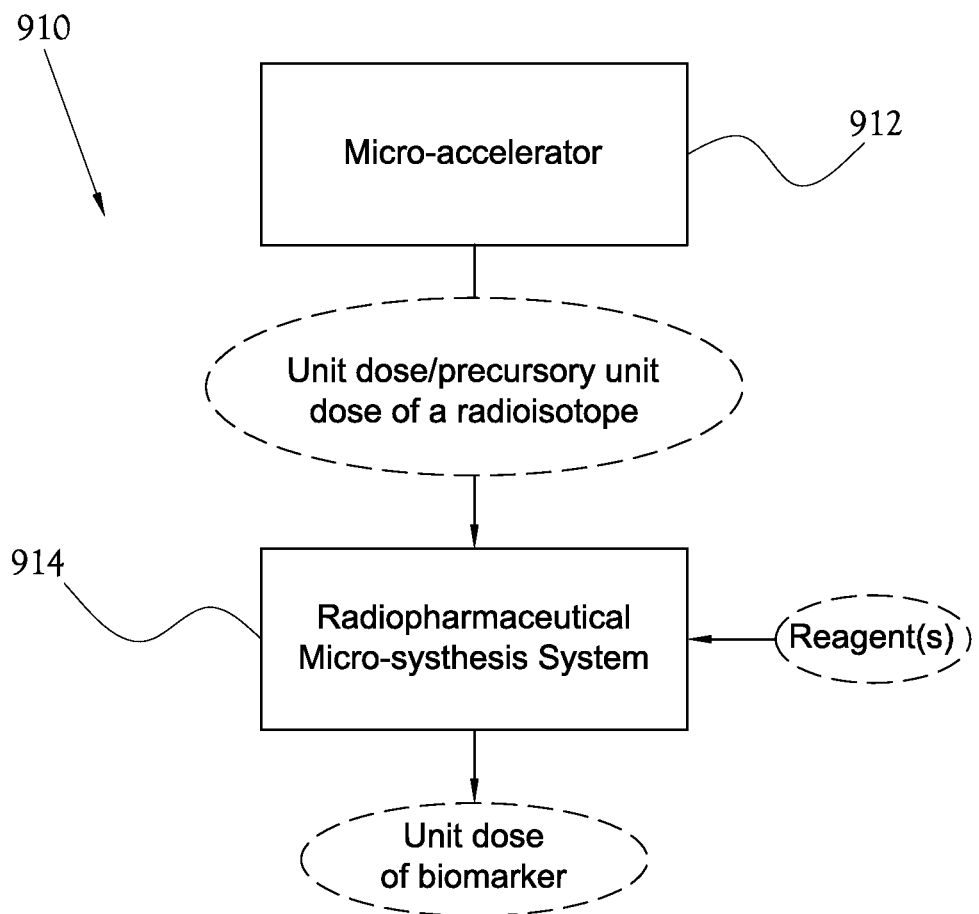
FIG. 9 is a block diagram of the improved biomarker generator described herein for producing a unit dose of a biomarker.

FIG. 9 illustrates one embodiment of the improved biomarker generator including a micro-accelerator 912 and a radiopharmaceutical micro-synthesis system 914, which as previous indicated incorporates at least one of a microreactor and microfluidic chip. As part of the complete improved biomarker generator, the radiopharmaceutical micro-synthesis system 914 will necessarily be configured to process the quantity of the radioisotope produced by the micro-accelerator 912. Microreactors and microfluidic chips typically perform their respective functions in less than 15 min, some in less than 2 min. This significant reduction in processing time directly allows a reduction in the quantity of the radioisotope required to synthesis the desired biomarker. A microfluidic chip exercises digital control over variables such as the duration of the various stages of a chemical process, which leads to a well-defined and narrow distribution of residence times. Such control also enables extremely precise control over flow patterns within the microfluidic chip. The use of a microfluidic chip facilitates the automation of multiple, parallel, and/or sequential chemical processes.

Figure 10:
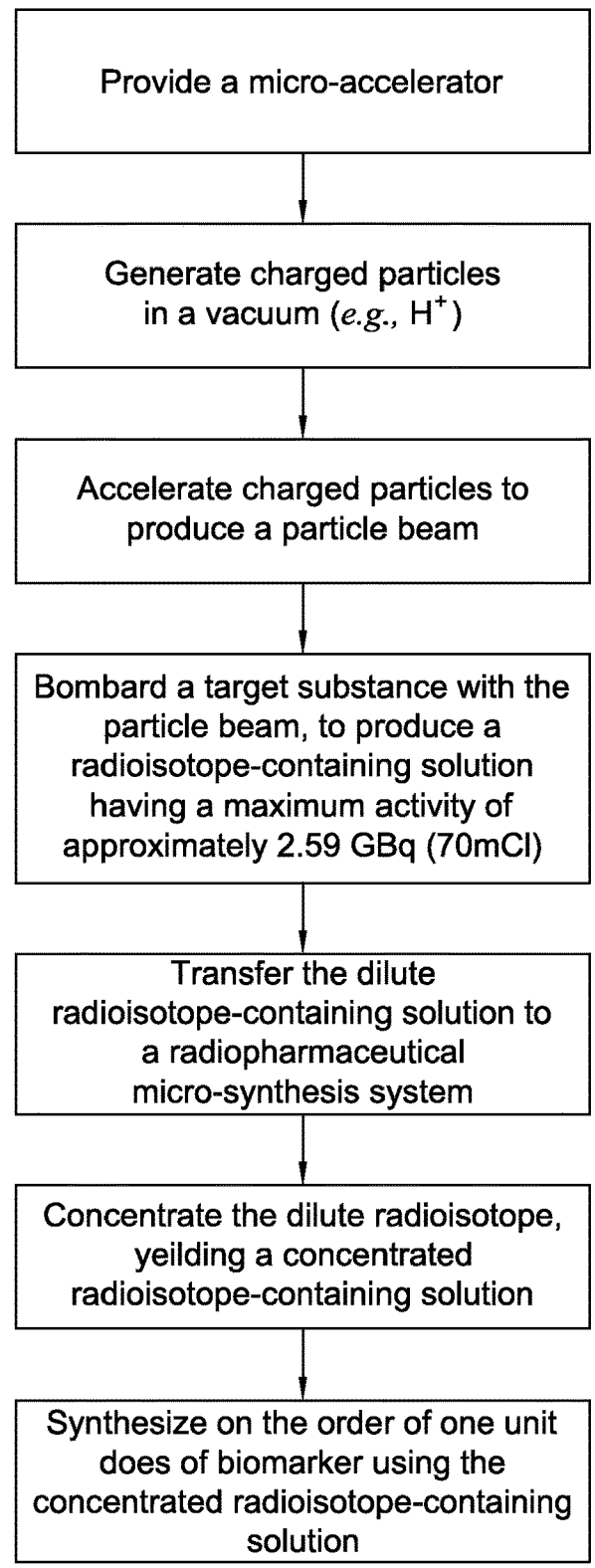
FIG. 10 is a flow diagram of one embodiment of the method for producing approximately one unit dose of a biomarker using the improved biomarker generator described herein.

FIG. 10 is a flow diagram of one embodiment of the method for producing a radiopharmaceutical using the improved biomarker generator. The method calls for providing a micro-accelerator, producing charged particles, accelerating the charged particles, and forming a particle beam to irradiate a target substance and produce a radioisotope. As an example, in the production of no-carrier-added fluorine-18, a particle beam of protons bombards the target substance of [$^{18}$O]water. The protons in the particle beam interact with the oxygen-18 isotope in the [$^{18}$O]water molecules. The improved biomarker generator allows operation using a volume of the target substance that is unusually small in the area of radiopharmaceutical production. A sufficient quantity of a fluorine-18 can be produced using a [$^{18}$O]water target substance with a volume of approximately 1 mL because the maximum mass of the radioisotope required to produce a unit dose of a radiopharmaceutical is on the order of nanograms. The internal target 183 discussed above is particularly well-suited for handling target substance volumes on this scale. While this example contemplates the use of a liquid target substance, one skilled in the art will recognize that certain methods of producing a radioisotope or radiolabeled precursor require an internal target that can accommodate a gaseous or solid target substance. Further, while the example given contemplates the production of fluorine-18, the internal target may be modified to enable the production of other radioisotopes or radiolabeled precursors, including [$^{11}$C]CO$_2$ and [$^{11}$C]CH$_4$, both of which are widely used in research. Such embodiments are considered to be within the scope and spirit of the present invention.

After irradiation, the radioisotope and at least one reagent are transferred to the radiopharmaceutical micro-synthesis system 114. The radioisotope undergoes processing such as concentration, as necessary. Ultimately, the radiopharmaceutical micro-synthesis system 114 combines the radioisotope with the reagent to synthesize the biomarker. In this context, a reagent is a substance used in synthesizing the biomarker because of the chemical or biological activity of the substance. Examples of a reagent include a solvent, a catalyst, an inhibitor, a biomolecule, and a reactive precursor. A reactive precursor is an organic or inorganic non-radioactive molecule that, in synthesizing a biomarker or other radiopharmaceutical, is reacted with a radioisotope, typically by nucleophilic substitution, electrophilic substitution, or ion exchange. The chemical nature of the reactive precursor varies and depends on the physiological process that has been selected for imaging. Exemplary organic reactive precursors include sugars, amino acids, proteins, nucleosides, nucleotides, small molecule pharmaceuticals, and derivatives thereof. Synthesis refers to the production of the biomarker by the union of chemical elements, groups, or simpler compounds, or by the degradation of a complex compound, or both. Synthesis, therefore, includes any tagging or labeling reactions involving the radioisotope and any processes (e.g., concentration, evaporation, distillation, enrichment, neutralization, and purification) used in producing the biomarker or in processing the target substance for use in synthesizing the biomarker. The latter is especially important in instances where (1) the volume of the target substance is too great to be manipulated efficiently within some of the internal structures of the radiopharmaceutical micro-synthesis system and/or (2) the concentration of the radioisotope in the target substance is lower than is necessary to optimize the synthesis reaction(s) that yield the biomarker. Accordingly, one embodiment of the radiopharmaceutical micro-synthesis system incorporates integrated separation components providing the ability to concentrate the radioisotope. Examples of suitable separation components include ion-exchange resins, semi-permeable membranes, or nanofibers. Such separations via semi-permeable membranes usually are driven by a chemical gradient or electrochemical gradient. Another example of processing the target substance includes solvent exchange. Continuing the example from above, the concentration of fluorine-18 obtained from a proton bombardment of [$^{18}$O]water is usually below 1 ppm. This dilute solution needs to be concentrated to approximately 100 ppm in order to optimize the kinetics of the biomarker synthesis reactions. This processing occurs in the radiopharmaceutical micro-synthesis system 114.

The improved biomarker generator enables the small scale in-situ production of a radioisotope and synthesis of biomarkers. Thus, the micro-accelerator 112 produces a sufficient quantity of the radioisotope for the radiopharmaceutical micro-synthesis system 114 to synthesize of the biomarker on the order of a unit dose of the biomarker. In one embodiment, the micro-accelerator 112 generates the radioisotope in a quantity on the order of a unit dose. In another embodiment, the micro-accelerator 112 generates the radioisotope in a quantity on the order of a precursory unit dose of the radioisotope. A precursory unit dose of the radioisotope is a dose of radioisotope that, after decaying for a length of time approximately equal to the time required to synthesize the biomarker, yields a quantity of biomarker having a quantity of radioactivity approximately equal to the unit dose appropriate for the particular class of patient or subject undergoing PET. For example, if the radiochemical synthesis system requires 20 min to synthesize a unit dose of a biomarker comprising carbon-11 ($t_{1/2}$=20 min), the precursory unit dose of the carbon-11 radioisotope has an radioactivity equal to approximately 200% times the radioactivity of a unit dose of the biomarker in order to compensate for the radioactive decay. Similarly, if the radiopharmaceutical micro-synthesis system requires 4 min to synthesize a unit dose of a biomarker labeled with oxygen-15 ($t_{1/2}$=2 min), the precursory unit dose of the oxygen-15 radioisotope has an radioactivity equal to approximately 400% times the radioactivity of a unit dose of the biomarker in order to compensate for the radioactive decay.

In some instances, the precursory unit dose of the radioisotope may be used to compensate for a radiopharmaceutical micro-synthesis system having a yield fraction that is significantly less than 100% of the radioactivity supplied. Further, the precursory unit dose may be used to compensate for radioactive decay during the time required in administering the biomarker to the patient or subject. One skilled in the art will recognize that the synthesis of a biomarker comprising a positron-emitting radioisotope should be completed within approximately the two half-lives of the radioisotope immediately following the production of the unit or precursory unit dose to avoid the significant increase in inefficiency that would otherwise result.

Figure 11:
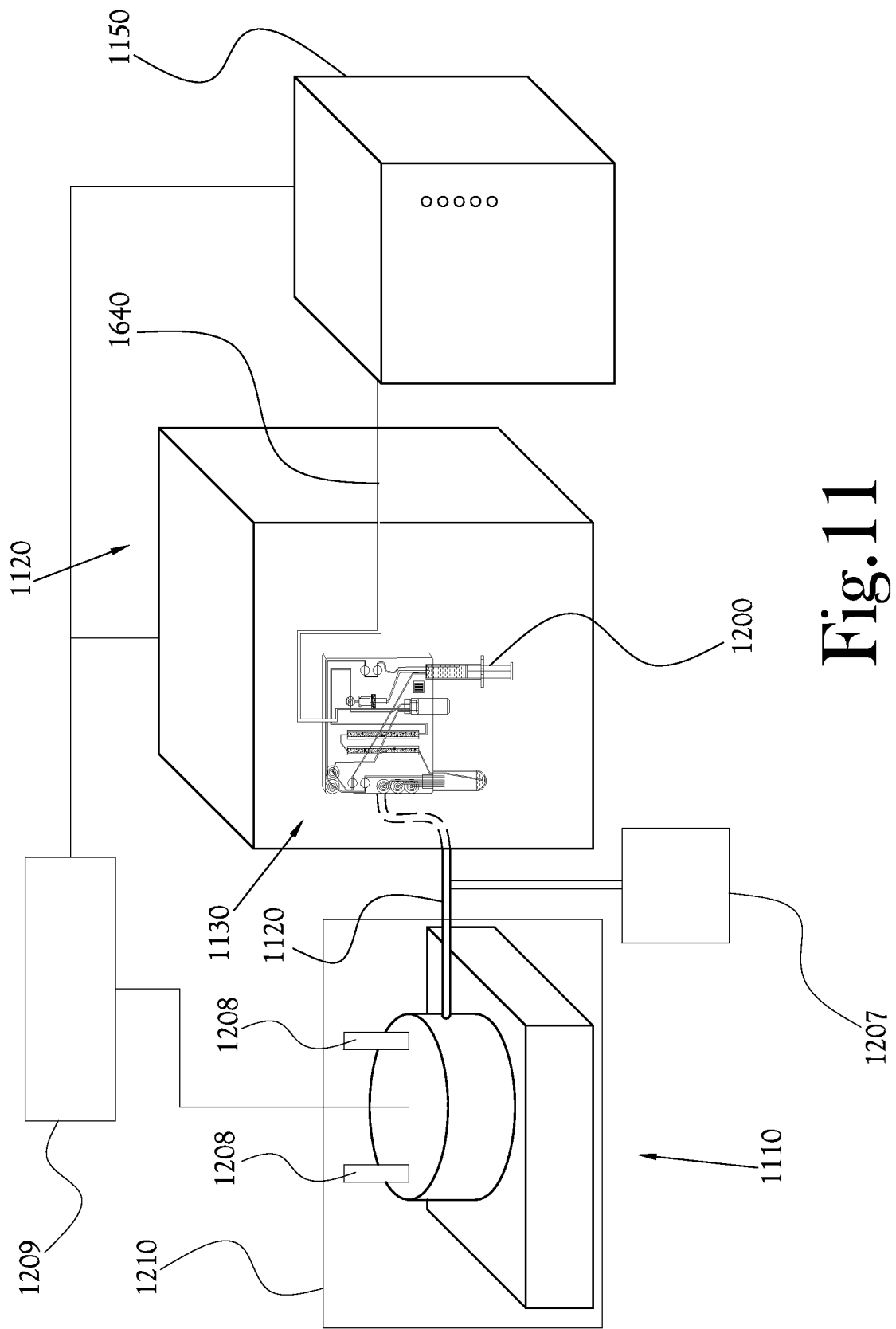
FIG. 11 is a schematic of the automated system which includes a computer which controls the cyclotron, synthesis system, and quality control system.

The chemical production module, the dose synthesis card and the sample card operate in conjunction with a complete PET biomarker production system. As shown in FIG. 11, one embodiment of this PET biomarker production system comprises an accelerator 1110, which produces the radioisotopes; a chemical production module (or CPM) 1120; a dose synthesis card 1130; a sample line 1640; and a quality control module (or QCM) 1150. Once the accelerator 1110 has produced a radioisotope, the radioisotope travels via a radioisotope delivery tube 1112 to the dose synthesis card 1130 attached to the CPM 1120. The CPM 1120 holds reagents and solvents that are required during the radiopharmaceutical synthesis process. In the dose synthesis card 1130, the radiopharmaceutical solution is synthesized from the radioisotope and then purified for testing and administration. Following synthesis and purification, a small percentage of the resultant radiopharmaceutical solution is the automated quality control system 1150, while the remainder flows into a dose administration vessel 1200. In some embodiments the quality control system can be a card based system and the syringe can be replaced by a vial. A computer 1209 controls all three systems and ensures that the system is capable of operating all three systems; cyclotron, synthesis system and quality control system simultaneously to ensure the most efficient workflow. The system can be also configured to accept manual injection, input, or introduction 1207 of a radioisotope from a separate cyclotron. The computer 1209 can also control multiple targets in the cyclotron and move them into the beam of the cyclotron independently to produce different radioisotopes. In some embodiments, the system can be configured with a vacuum pump to optimize the synthesis process and yield of the radiopharmaceutical. The system will have a shield around the cyclotron which is some embodiments is less than 11 feet in diameter and reduces the radiation field around the cyclotron to such a level that it is safe for a radiation worker to be present (typically <1 mrem/hr) to be present in the workspace 1210 around the accelerator 1110.

Figure 12:
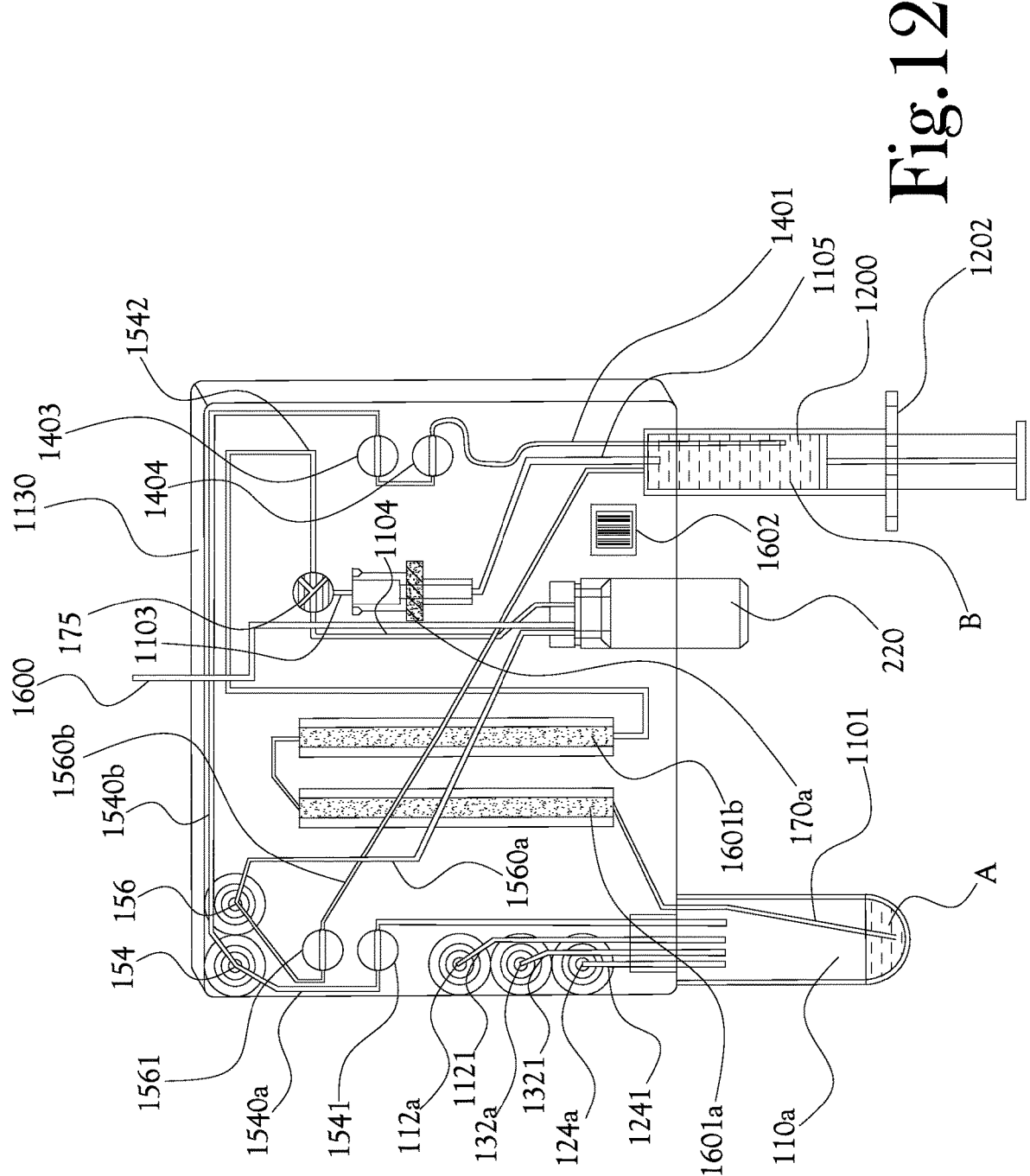
FIG. 12 is a schematic illustration of an embodiment of the dose synthesis card which only has a connection line to QC system and no sample card.
Figure 13:
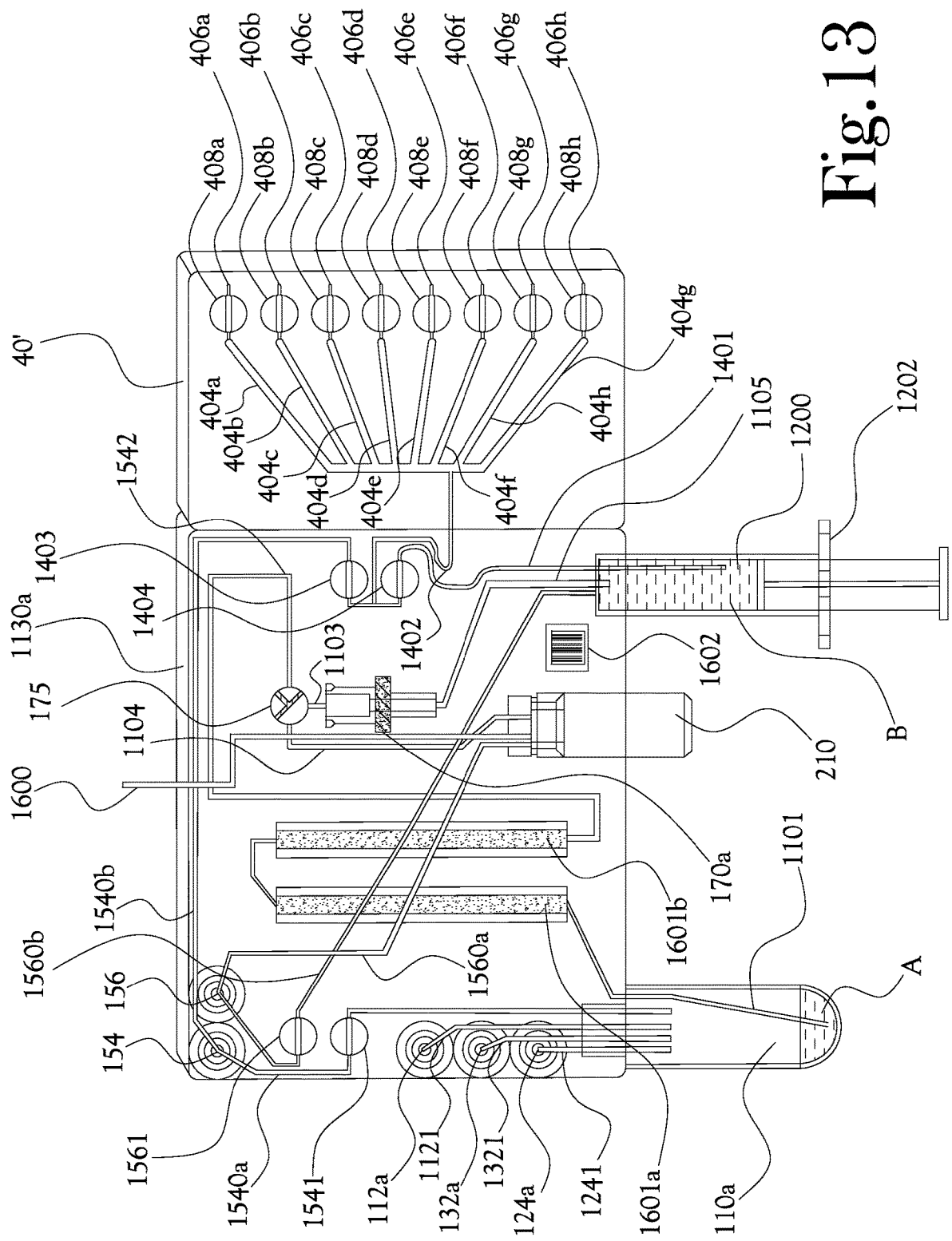
FIG. 13 is a schematic illustration of a automated radiopharmaceutical production system with automated QC which does not require a sample card.

FIG. 12 is an embodiment of the dose synthesis card with no sample card and only a QC draw line 1600. FIG. 13 displays a schematic view of one embodiment of the dose synthesis card 30' together with an attached sample card 40'. The necessity for a sample card is dependent on the radiopharmaceutical used for production.

As shown in FIG. 12, in one illustrated example embodiment, a dose synthesis card 30' includes a reaction vessel 110a where the radiopharmaceutical solution is synthesized, a QC draw line 1600 for automatic extraction of QC sample, and a RF ID chip or barcode for radiopharmaceutical identification, 1602. The purpose of the RF ID chip or barcode is to uniquely identify the type of radiopharmaceutical that is being produced so that a user does not mistakenly produce a radiopharmaceutical which is incompatible with the card. A radioisotope input 112a introduces the radioisotope F-18 into the reaction vessel 110a through a radioisotope input channel 1121. At this stage, the radioisotope is still mixed with quantities of heavy water from the biomarker generator. Next, an organic input 124a introduces a solution of potassium-kryptofix complex in acetonitrile into the reaction vessel 110a through an organic input channel 1241. A combination nitrogen-input and vacuum 154 pumps nitrogen gas into the reaction vessel 110a through a gas channel 1540a and a valve 1541, which valve is at that time in an open position. The mixture A in the reaction vessel 110a is heated in nitrogen atmosphere to azeotropically remove water from the mixture A, the vaporized water being evacuated through the gas channel 1540a and the vacuum 154. Next, the organic input 124a introduces mannose triflate in dry acetonitrile into the reaction vessel 110a through the organic input channel 1241. The solution is heated at approximately 110 degrees Celsius for approximately two minutes. By this stage, the F-18 has bonded to the mannose to form the immediate precursor for [$^{18}$F]FDG, FTAG. Next, aqueous hydrochloric acid is introduced into the reaction vessel 110a through an aqueous input 132a and an aqueous channel 1321. The hydrochloric acid removes the protective acetyl groups on the intermediate $^{18}$F-FTAG, leaving $^{18}$F-fludeoxyglucose (i.e. [$^{18}$F]FDG).

Having been synthesized, the [$^{18}$F]FDG in solution passes from the reaction vessel 110a through a post-reaction channel 1101 into a solid phase extraction column 160a, where some undesirable substances are removed from the solution, thereby clarifying the radiopharmaceutical solution. In some embodiments of the present invention, the solid phase extraction (SPE) column 160a comprises a length with an ion exchange resin, a length filled with alumina, and a length filled with carbon-18. The radiopharmaceutical passes through the purification component column 160a and in some embodiments passes through a second purification component 1601 with a mobile phase that in many embodiments includes acetonitrile from the organic input 124a. The purification components 160a 1601 can be single phase extraction components or trap and release purification components depending on the radiopharmaceutical. As some of the mobile phase and impurities emerge from the SPE column 160a, they pass through a second post-reaction channel 1542 and through a three-way valve 175 and waste channel 1104 into a waste receptacle 210. As the clarified radiopharmaceutical solution emerges from the SPE column 160a, the radiopharmaceutical solution next passes through the second post-reaction channel 1542 and through the three-way valve 175 into a filter channel 1103 and then through a filter 170a. The filter 170a removes other impurities (including particulate impurities), thereby further clarifying the radiopharmaceutical solution. In many embodiments the filter 170a includes a Millipore filter with pores approximately 0.22 micrometers in diameter.

Once the radiopharmaceutical solution has passed through the filter 170a, the clarified radiopharmaceutical solution travels via the post-clarification channel 1105 into the sterile dose administration vessel 1200, which in the illustrated embodiment is incorporated into a syringe 1202 or a collection vial. In some embodiments, the dose administration vessel is filled beforehand with a mixture of phosphate buffer and saline.

FIG. 13 displays a schematic view of one embodiment of the dose synthesis card 30' together with the attached sample card 40'. As the clarified radiopharmaceutical solution fills the sterile dose administration vessel 1200, some of the solution B is diverted through an extraction channel 1401, an open valve 1403, and a transfer channel 1402 into the sample card 40'. The sample card 40' contains a number of sample loops 404a-h, which hold separated aliquots of solution for imminent testing, and a number of valves 408a-h, which at this stage are closed. Once the test-sample aliquots of radiopharmaceutical solution are collected, the sample card 40' is separated from the dose synthesis card 30' and inserted into the QCM. The aliquots then travel through the now-open valves 408a-h into the sample egress ports 406a-h, from which the aliquots pass into the test vessels, as was shown in FIG. 4. In the some embodiments, each of the sample loops 404a-h holds approximately 10 microliters of sample solution. The number of sample loops will vary according to the number of quality control tests to be performed for that run, and the system is adapted to operate with different sample cards containing varying numbers of sample loops. After the sample aliquots pass into the sample card 40', any excess solution remaining in the dose administration vessel 1200 is extracted by a vent 156 through a first venting channel 1560b and thence conveyed through an open valve 1561 and through a second venting channel 1560a into the waste receptacle 210. The vacuum 154 evacuates residual solution from the transfer channel 1402 through a now-open valve 1403 and a solution evacuation channel 1540b.

In some embodiments of the present invention, the CPM holds sufficient amounts of reagents and solvents that are required during the radiopharmaceutical synthesis process to carry out multiple runs without reloading. Indeed, in some embodiments the CPM is loaded with reagents and solvents approximately once per month, with that month's supply of reagents and solvents sufficient to produce several dozen or even several hundred doses of radiopharmaceutical. As the reagents and solvents are stored in the CPM, it is easier than under previous systems to keep the reagents and solvents sterile and uncontaminated. In some embodiments, a sterile environment is supported and contamination inhibited by discarding each dose synthesis card and the sample card after one run; these components of the system are adapted to be disposable.

Figure 14A:
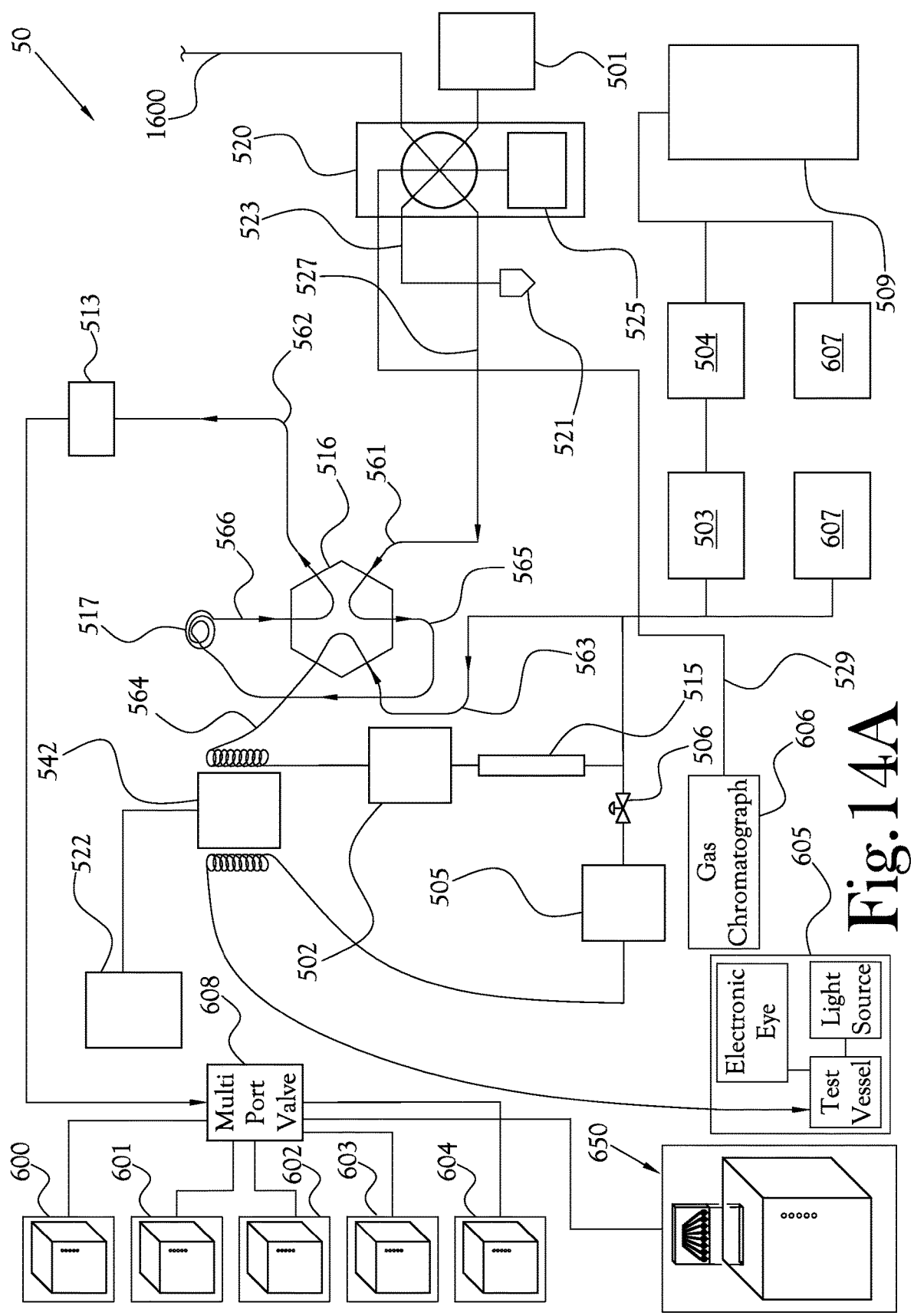
FIG. 14A is a flow diagram showing a fully automated QC system which tests for all pharmacopeia (e.g. regulatory requirements) using a multi-port switching valve to distribute the sample to a number of additional pieces of equipment.

FIG. 14A is a flow diagram showing a fully automated QC system which tests for all pharmacopeia (e.g. regulatory requirements) using a multi-port switching valve to distribute the sample to a number of additional pieces of equipment. During the quality control testing process, at a point where sample radiopharmaceutical solution is flowing from the syringe-pump assembly 520 through the pH detector 501 and through the first injection valve line 561, the injection valve 516 is rotated 60 degrees into the second state (or State B), shown in FIG. 14. In State B, the sample radiopharmaceutical solution passes from the first injection valve line 561, through the injection valve 516, and then into the fifth injection valve line 565; from the fifth injection valve line 565, the sample radiopharmaceutical solution enters the fixed-volume fluid loop 517. As fluid continues to flow while the injection valve 516 is in State B, sample radiopharmaceutical solution flowing through the fixed-volume fluid loop 517 exits the fixed-volume fluid loop 517 and re-enters the injection valve 516 through the sixth injection valve line 566; the sample radiopharmaceutical solution is then directed into the second injection valve line 562, and the sample radiopharmaceutical solution passes through the second injection valve line 562 to the pH detector 513 and the waste vessel 507.

While sample radiopharmaceutical solution is flowing through the fixed-volume fluid loop 517, the injection valve 516 is rotated a second time, so that the injection valve is again in State A. At this point in time, mobile phase solvent from the HPLC pump 503 passes through the third injection valve line 563 and into the injection valve 516; within the injection valve 516, the mobile phase solvent from the third injection valve line 563 is directed into the fifth injection valve line 565. The mobile phase solvent within the fifth injection valve line 565 enters the fixed-volume fluid loop 517, pushing the sample radiopharmaceutical solution within the fixed-volume fluid loop 517 out of the fixed-volume fluid loop 517 and through the sixth injection valve line 566 into the injection valve 516. Within the injection valve 516, the sample radiopharmaceutical solution from the fixed-volume fluid loop 517 is directed into the fourth injection valve line 564. (In some embodiments, the fixed-volume loop 517 has a volume of approximately 20 microliters. However, those of skill in the art will recognize that other volumes the fixed-volume loop 517 are possible and are contemplated by the present invention.)

Conveyed along the fourth injection valve line 564, the sample radiopharmaceutical solution from the fixed-volume fluid loop 517 passes by at least one radiation probe 542, which is part of or connected to a radiation detector 522. Next, the sample radiopharmaceutical solution passes by or through a UV/VIS detector 502 to test the optical clarity of the sample radiopharmaceutical solution. In some embodiments, the UV/VIS detector 502 comprises a ultra-violet and visible light spectrometer. In some embodiments, the UV/VIS detector 502 comprises a UV spectrophotometer. In some embodiments, the UV/VIS detector 502 comprises a UV spectrophotometer with a deuterium light source. In some embodiments, the UV/VIS detector 502 comprises a UV spectrophotometer with a tungsten-halogen light source. In some embodiments, the UV/VIS detector 502 comprises a UV spectrophotometer like the Smartline UV Detector 2500, manufactured by KNAUER. In some embodiments, the HPLC-based QCM 50 includes a detector comprises a spectrophotometer that detects a range of the electromagnetic spectrum that includes infrared light. In some embodiments, the HPLC-based QCM 50 includes multiple detectors, including, in some embodiments, multiple UV/VIS detectors or, in some embodiments, multiple spectrophotometers or spectrometers.

In some embodiments, the UV/VIS detector 502 tests the sample radiopharmaceutical solution for the presence of residual Krypotofix. Generally, a purified radiopharmaceutical solution will be considered to pass quality control testing for Kryptofix if the residual concentration of Kryptofix in the final product is less than or equal to 50 micrograms per milliliter solution.

In some embodiments, the radiopharmaceutical solution from the fixed-volume fluid loop 517 passes by or through the UV/VIS detector 502 before entering the HPLC column 515. In In some embodiments, the radiopharmaceutical solution from the fixed-volume fluid loop 517 passes by or through a UV/VIS detector after entering and passing though the HPLC column 515.

After passing by or through the UV/VIS detector 502, the sample radiopharmaceutical solution passes into the HPLC column 515. The HPLC column 515 separates [$^{18}$F]FDG within the sample radiopharmaceutical solution from any other radioactive products or other organic impurities. In this way, the HPLC column 515 assists testing the radiochemical identity of the sample radiopharmaceutical solution—that is, the HPLC column 515 helps to identify the ratio of [$^{18}$F]FDG (or other desired radiopharmaceutical compound) to other radioactive products (such as free F-18 ion and [$^{18}$F]FTAG). The HPLC column 515 separates the [$^{18}$F]FDG from other compounds based on their different retention time, making possible the identification of the [$^{18}$F]FDG based on retention time and allowing other instruments to analyze the [$^{18}$F]FDG separately from other compounds. Thus, in some embodiments, after exiting the HPLC column 515, the sample radiopharmaceutical solution passes through a refractive index detector (RI detector) 505. The RI detector 505 detects, measures and quantifies the presence of compounds as they are eluted from the HPLC column 515. [$^{18}$F]FDG is identified based on its retention time, as are other compounds present in the sample radiopharmaceutical solution. In general, [$^{18}$F]FDG has a slightly shorter retention time compared to FDG that lacks a radioisotope. In some embodiments, the radiochemical purity of the separated [$^{18}$F]FDG within the sample radiopharmaceutical solution is also measured after the elution of the separated [$^{18}$F]FDG within the sample radiopharmaceutical solution from the HPLC column 515.

In many embodiments, the RI detector 505 also measures the residual concentration in the sample radiopharmaceutical solution of solvents such as acetonitrile and ethanol. Generally, a purified radiopharmaceutical solution will be considered to pass quality control testing if the residual concentration of acetonitrile in the sample radiopharmaceutical solution is less than or equal to 400 ppm.

As shown in FIG. 14, in some embodiments, an HPLC-based QCM 50 according to the present general inventive concept includes a radiation detector 522 with at least one radiation probe 542. In some embodiments, multiple HPLC-based QCM pumps and columns can be used as shown in FIG. 6 503, 504, 607. As shown in FIGS. 4 and 5, the radiation probe 542 measures the radioactivity of the separated [$^{18}$F]FDG within the sample radiopharmaceutical solution eluted from the HPLC column 515. The radiation probe 542 also measures the radioactivity of other radioactive products (such as free F-18 ion and [$^{18}$F]FTAG) eluted from the HPLC column 515.

Generally, after the sample radiopharmaceutical solution is eluted from the HPLC column 515 and tested for radiochemical identity, radiochemical purity, and the presence of residual impurities, the sample radiopharmaceutical solution is conveyed to the waste vessel 507. In some embodiments, HPLC-based QCM 50 according to the present general inventive concept also includes, on the line carrying the sample radiopharmaceutical solution from the HPLC column 515 to the waste vessel 507, a backpressure valve 506.

FIG. 14A illustrates an embodiment of the automated quality control system which has a multiport valve 608 to distribute said radiopharmaceutical sample to additional QC equipment for quality control testing including; a phase transfer catalyst device 600, a multi channel analyzer for radionucleic purity and identity 600, a dose calibrator for radioactivity level measurements 608, a endotoxin measurement device 602 which in some embodiments can be a Charles River Sample tester, a color metric device 603, for color and clarity testing, a sample card system for additional QC testing 604, an electronic eye device the measure the electronic conductivity of said radiopharmaceutical 605, a gas chromatraphy system for residual solvent identification 606, and parallel HPLC pumps and columns 503, 504, 607 which is some embodiments can be in series.

Figure 14B:
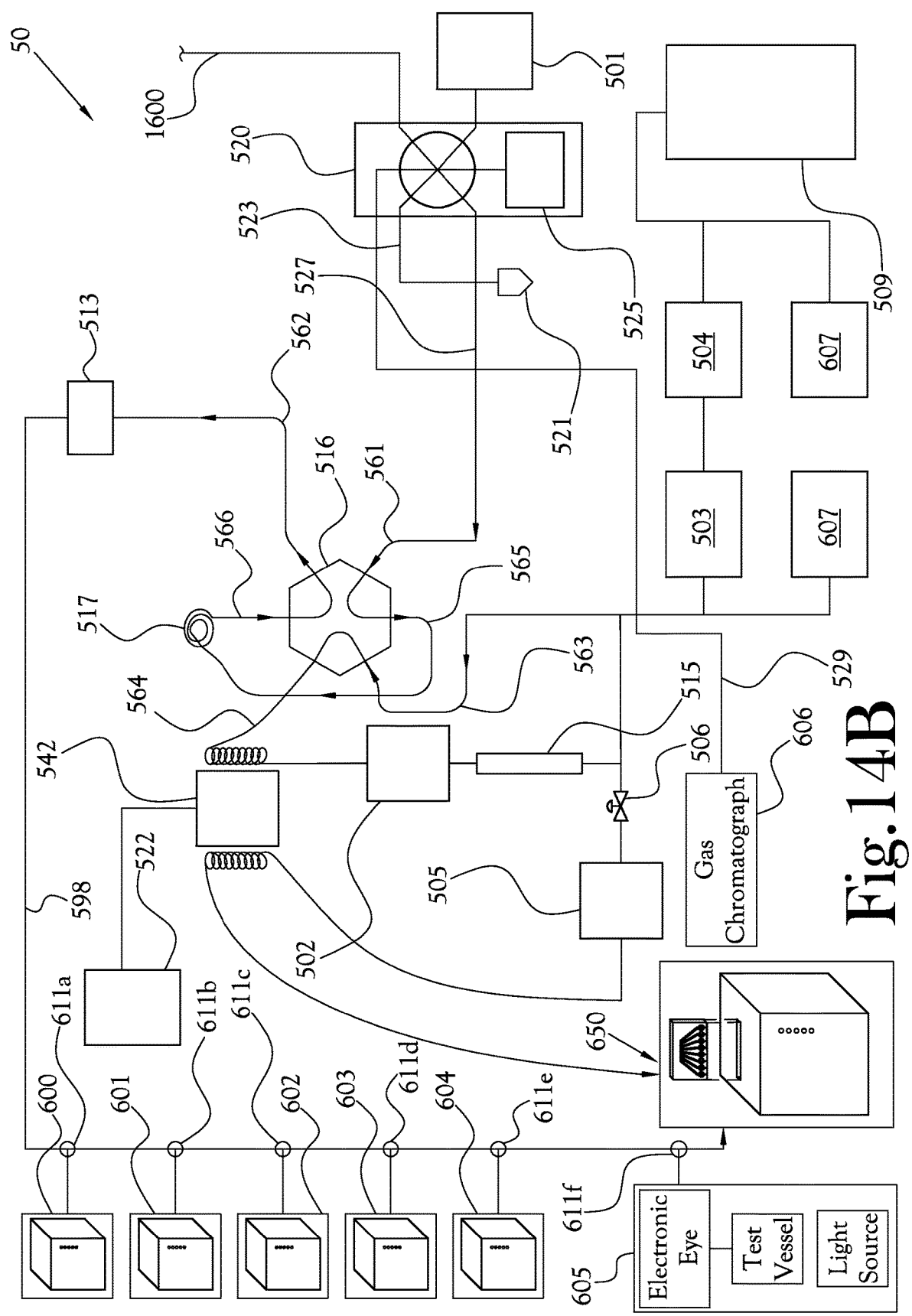
FIG. 14B is a fourth flow diagram showing a fully automated QC system which tests for all pharmacopeia (e.g. regulatory requirements) using a series of load loops or ports to draw samples for a number of additional pieces of equipment from a sample line.

FIG. 14B illustrates another embodiment of the automated quality control system which has a sample line 598 with a number of load loops or ports 611a-f arranged in series, with each load loop or port diverting a portion of radiopharmaceutical solution from the sample line 598 to a testing device; each testing device thus draws a small sample volume of radiopharmaceutical solution from the total amount of radiopharmaceutical solution passing through the sample line 598. In the illustrated example embodiment shown in FIG. 6B, the testing devices include: a phase transfer catalyst device 600; a multi-channel analyzer for radionucleic purity and identity 601; a dose calibrator for radioactivity level measurements 602; a endotoxin measurement device 603 (which in some embodiments can be a Charles River Sample tester); a color metric device 604 for color and clarity testing; and an electronic eye device the measure the electronic conductivity of said radiopharmaceutical 605. In the illustrated example shown in FIG. 6B, the sample line 598 terminates in sample card system for additional QC testing 650; but those of skill in the art will recognized that other arrangements are also possible and are encompassed by the present general inventive concept. Further, in some embodiments, additional testing devices "feed off of" (i.e., received sample radiopharmaceutical solution from) the sample line 598; in some embodiments, these testing devices may include, for example, a gas chromatraphy system for residual solvent identification.

In some embodiments of the present general inventive concept, where the system in use includes a component or components for detecting the presence of residual phase transfer catalyst in the finished radiopharmaceutical solution, an iodine reagent is mixed with a sample solution containing the phase transfer catalyst Kryptofix 2.2.2; this mixture causes a red suspension to form, which can be observed visually. The concentration of Kryptofix 2.2.2 in the solution is proportional to the color intensity of the suspension, and visual differences were observed for solutions having a Kryptofix 2.2.2 concentration in the range of 0 to 100 ppm.

In some embodiments, the iodine reagent and the sample solution containing Kryptofix 2.2.2 are mixed together before the mixture is passed through the detector chamber or the iodine reagent and the sample solution containing Kryptofix 2.2.2 are mixed together inside the detector chamber. Next, the mixture enters the detector chamber. The presence or absence of suspension is determined visually, and the absorbance is measured with a detector. The concentration of Kryptofix 2.2.2 in the mixture is determined by comparing the absorbance results with a calibration curve obtained from test solutions having known Kryptofix 2.2.2 concentrations.

In general, the subsystem used to determine the concentration of the phase transfer catalyst comprises reservoirs for the sample and iodine solutions connected to a metering device and a UV-Vis cell or microfluidic chip with a clear window for detection. In some embodiments, the phase transfer catalyst is Kryptofix 2.2.2. Overall, the present general inventive concept permits concentration determination having the following characteristics: simplicity, specificity, low toxicity, and high throughput, which are desirable for [18F]-labeled radiotracers owing to the relatively short half-life of the [18F] isotope (109 min).

In some embodiments, the iodine reagent is mixed with a sample solution containing Kryptofix 2.2.2, which causes a red suspension to form. The concentration of Kryptofix 2.2.2 in the solution is proportional to the color of the suspension. In some embodiments, the iodine reagent and the sample solution containing Kryptofix 2.2.2 are mixed together before the mixture is passed through the detector chamber. Next, the mixture enters the detector chamber. The presence or absence of suspension is determined visually, and the absorbance is measured with a detector. The concentration of Kryptofix 2.2.2 in the mixture is determined by comparing the absorbance results with a calibration curve obtained from test solutions having known Kryptofix 2.2.2 concentrations.

Although the foregoing description emphasizes the production of biomarkers labeled with fluorine-18, such as [$^{18}$F]FDG, the radiopharmaceutical micro-synthesis system is flexible and may be used to synthesize biomarkers labeled with other radioisotopes, such as carbon-11, nitrogen-13, or oxygen-15. Further, the improved biomarker generator discussed herein is flexible enough to produce quantities on the order of a unit dose of biomarkers that are labeled with radioisotopes that do not emit positrons or for producing small doses of radiopharmaceuticals other than biomarkers. One skilled in the art will recognize also that the radiopharmaceutical micro-synthesis system may comprise parallel circuits, enabling simultaneous production of unit doses of a variety of biomarkers. Finally, one skilled in the art will recognize that the improved biomarker generator may be engineered to produce unit doses of biomarker on a frequent basis.

From the foregoing description, it will be recognized by those skilled in the art that an improved biomarker generator has been provided. The improved biomarker generator described herein allows for the nearly on-demand production of a biomarker in a quantity on the order of one unit dose. Because the half-lives of the radioisotopes most suitable for safe molecular imaging of a living organism are very short, nearly on-demand production of unit doses of biomarkers presents a significant advancement for both clinical medicine and biomedical research. The reduced size, weight, and cost, the reduced infrastructure (power and structural) requirements, and the improved reliability of the micro-accelerator coupled with the speed and overall efficiency of the radiopharmaceutical micro-synthesis system make in-house biomarker generation a viable option even for small regional hospitals. The various embodiments of the micro-accelerator generate the magnetic field using permanent magnets, move the target into the magnetic field allowing the magnet system to help contain radiation generated during radioisotope production, incorporate the improved RF system described herein, and use combinations of these features to provide the aforementioned improvements over conventional cyclotrons used in radiopharmaceutical production.

A system according to the present general inventive concept allows for automated sampling and analysis of a radiopharmaceutical solution in real time. In some embodiments, a cyclotron, chemical production module, and quality control module are all controlled by the same computer, and all three component subsystems (cyclotron, chemical production module, and quality control module) run simultaneously, in series or in parallel. In some embodiments, for example, while a CPM is producing dose N in a series of doses, the QCM is analyzing dose N-1 (said dose N-1 having just emerged from the CPM), and the cyclotron is simultaneously producing the radioisotopes to go into dose N+1. Such a setup helps to streamline the process of generating radiopharmaceutical doses. Some embodiments include automating the entire workflow. Various embodiments of systems according to the present general inventive concept also facilitate the use of small target volumes for radioisotope precursor target materials.

While the present invention has been illustrated by description of several embodiments and while the illustrative embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative apparatus and methods, and illustrative examples shown and described. Accordingly, departures may be made from such details without departing from the spirit or scope of applicant's general inventive concept.

What is claimed is:

1. An automated radiopharmaceutical production and quality control system for automatically producing a quantity of radiopharmaceutical on an order of up to ten unit doses, said system comprising:
   a computer that receives a selection input identifying a selected radiopharmaceutical;
   a cyclotron in communication with said computer, said cyclotron to produce a radioisotope associated with said selected radiopharmaceutical, said cyclotron initiating production of the radioisotope upon receiving computer activating; and
   a chemical production subsystem to transfer, synthesize, and purify said radioisotope into a maximum quantity of a radiopharmaceutical on the order of up to ten unit doses using a disposable microfluidic radiopharmaceutical synthesis card;
   said disposable microfluidic radiopharmaceutical synthesis card including:
      at least one reaction vessel configured to receive a radioisotope and at least one reagent, said reaction vessel being configured to receive energy from an energy source, whereby when said radioisotope and said at least one reagent are mixed in said reaction vessel and energy is provided to said reaction vessel from said energy source, a radiopharmaceutical is synthesized;
at least one purification component to purify said radiopharmaceutical; and
a vessel adapted to receive said radiopharmaceutical following the passage of said radiopharmaceutical through said purification component;
a draw line connected between said disposable microfluidic radiopharmaceutical synthesis card and an automated quality control system for radiopharmaceuticals, said draw line configured to extract at least one small volume of said radiopharmaceutical from said disposable microfluidic radiopharmaceutical synthesis card and to transfer said at least one small volume to said an automated quality control system for radiopharmaceuticals, said automated quality control system for radiopharmaceuticals to test the radiopharmaceutical to ensure that it is safe for injection, said an automated quality control system for radiopharmaceuticals comprising:
a high performance liquid chromatography column and a radiation probe to measure the radioactivity of said radiopharmaceutical, said high performance liquid chromatography column to receive a first portion of the at least one small volume of said radiopharmaceutical from said draw line; and
a sample line and a multi-port switching valve to receive a second portion of said at least one small volume from said draw line and to distribute sample volumes of said second portion to multiple analytical testing devices to perform various quality control tests on the radiopharmaceutical,
wherein the multiple analytical testing devices receiving sample volumes from said multi-port switching valve are able to conduct tests on the sample volumes of radiopharmaceutical from the second portion while the first portion is passing through said high performance liquid chromatography column,
wherein said cyclotron, said chemical production subsystem and said automated quality control system for radiopharmaceuticals are all controlled by said computer,
wherein said cyclotron, said chemical production subsystem and said automated quality control system for radiopharmaceuticals run simultaneously in series or in parallel, and
wherein while said chemical production subsystem is producing dose N in a series of doses, said automated quality control system for radiopharmaceuticals is analyzing dose N−1, said dose N−1 having just emerged from said chemical production subsystem and said cyclotron is simultaneously producing said radioisotope to go into dose N+1.

2. The system of claim 1., wherein said cyclotron produces said radioisotope associated with said selected radiopharmaceutical by locating a target substance in a magnetic field generated by said cyclotron and bombarding said target substance with said particle beam without said particle beam exiting said magnetic field.

3. The system of claim 1, wherein said radioisotope associated with said selected radiopharmaceutical is $^{18}$F, $^{11}$C, $^{124}$I, $^{13}$N, $^{15}$O, or $^{68}$Ga.

4. The system of claim 1, wherein said selected radiopharmaceutical is produced in a specified maximum quantity determined by a level of radioactivity of said quantity, and wherein said selected radiopharmaceutical and the level of radioactivity is selected from the group consisting of [18F] 2-fluoro-2-deoxy-D-glucose with a maximum radioactivity level of approximately 250 mCi, [18F]Sodium Flouride with a maximum radioactivity level of approximately 250 mCi, [18F]fluoromisonidazole with a maximum radioactivity level of approximately 170 mCi, [18F] 3'-deoxy-3'fluorothymidine with a maximum radioactivity level of approximately 170 mCi, [18F] fluorocholine with a maximum radioactivity level of approximately 60 mCi, [18F]Fallypride with a maximum radioactivity level of approximately 250 mCi, [18F]Florbetaben with a maximum radioactivity level of approximately 180 mCi, [18F]Florbetapir with a maximum radioactivity level of approximately 300 mCi, [18F]-fluoro-ethyl-tyrosine with a maximum radioactivity level of approximately 200 mCi, [18F]flutemetamol with a maximum radioactivity level of approximately 150 mCi, [18F]FDOPA with a maximum radioactivity level of approximately 200 mCi, [11C]Choline with a maximum radioactivity level of approximately 100 mCi, [11C]acetate with a maximum radioactivity level of approximately 450 mCi, [11C]N-Methylspiperone with a maximum radioactivity level of approximately 200 mCi, [11C]Carfentanil with a maximum radioactivity level of approximately 100 mCi, and [11C]Raclopride with a maximum radioactivity level of approximately 100 mCi.

5. The system of claim 1 wherein said cyclotron has a maximum beam power selected from the group consisting of 50 W, 75 W, 100 W, 125 W, 150 W, 175 W, and 200 W.

6. The system of claim 5, wherein said cyclotron produces the radioisotope associated with said selected radiopharmaceutical with a beam of charged particles having an average energy within a range selected from the group consisting of 5 MeV to 18 MeV, 5 MeV to 10 MeV, 7 MeV to 10 MeV, 8 MeV to 10 MeV, and 7 MeV to 18 MeV.

7. The system of claim 6, wherein said average energy of said charged particles is in the range of 5 MeV to 10 MeV.

8. The system of claim 6, wherein said charged particles are selected from the group consisting of protons and deuterons and wherein said average energy of said charged particles is in the range of 5 MeV to 10 MeV and said maximum beam power is 200 W.

9. The system of claim 1, wherein said computer prints out a dose record summarizing the results of the quality control tests.

10. The system of claim 1, wherein said system simultaneously manages manufacture of said radioisotope, production of said radiopharmaceutical and quality control of said radiopharmaceutical.

11. The system of claim 1, wherein said system activates an ion source which generates a beam of charged particles accelerated through a magnetic and electric field to an energy greater than or equal to a nuclear binding energy of a target substance.

12. The system of claim 11, wherein said system selects the target substance for said radioisotope of said radiopharmaceutical.

13. The system of claim 12, wherein said charged particles hitting said target substance produces a selected radioisotope.

14. The system of claim 13, wherein said system generating said beam of charged particles with a maximum beam power of 200 W, said charged particles selected from the group consisting of protons and deuterons, and said charged particles accelerated to an average energy at least equal to the nuclear binding energy of said target substance.

15. The system of claim 14, wherein said system produces said radioisotope in a maximum quantity per production run on an order of up to ten unit doses from said target substance by bombarding said target substance with said charged particles.

16. The system of claim 15, wherein said target substance associated with said radiopharmaceutical is moved into said beam of charged particles by said computer.

17. The system of claim 1, wherein said system receives said radioisotope from manual injection into said disposable microfluidic radiopharmaceutical synthesis card.

18. The system of claim 1, wherein said system has a vacuum pump attached to a vent line of said disposable microfluidic radiopharmaceutical synthesis card to remove vapor formation.

19. The system of claim 1, wherein said disposable microfluidic radiopharmaceutical synthesis card includes an RF ID chip or bar code to identify said radiopharmaceutical associated with said disposable microfluidic radiopharmaceutical synthesis card.

20. The system of claim 1, wherein said system has a shield around the cyclotron reducing a radiation field outside the shield to acceptable levels of (<1 mrem/hr).

\* \* \* \* \*

UNITED STATES PATENT AND TRADEMARK OFFICE
CERTIFICATE OF CORRECTION

| | | |
|---|---|---|
| PATENT NO. | : 11,135,321 B2 | Page 1 of 1 |
| APPLICATION NO. | : 14/618795 | |
| DATED | : October 5, 2021 | |
| INVENTOR(S) | : Mark Khachaturian et al. | |

It is certified that error appears in the above-identified patent and that said Letters Patent is hereby corrected as shown below:

On the Title Page

Item (73) recites the Assignee as "Best Medical International, Inc., Springfield VA (US)" and should be corrected to read -- Best ABT, Inc., Springfield VA (US) --.

Signed and Sealed this
Fifteenth Day of November, 2022

Katherine Kelly Vidal
*Director of the United States Patent and Trademark Office*